(12) United States Patent
Murray, III

(10) Patent No.: US 12,708,538 B2
(45) **Date of Patent: *Aug. 18, 2026**

(54) PROSTHESIS DELIVERY SYSTEM WITH TIP TRAVEL LIMITER AND METHOD OF USE

(71) Applicant: Medtronic Vascular, Inc., Santa Rosa, CA (US)

(72) Inventor: Robert J. Murray, III, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 1399 days.

This patent is subject to a terminal disclaimer.

(21) Appl. No.: 17/407,408

(22) Filed: Aug. 20, 2021

(65) Prior Publication Data

US 2021/0378852 A1 Dec. 9, 2021

Related U.S. Application Data

(63) Continuation of application No. 15/939,353, filed on Mar. 29, 2018, now Pat. No. 11,123,208.

(51) Int. Cl.
*A61F 2/966* (2013.01)
*A61F 2/07* (2013.01)
(Continued)

(52) U.S. Cl.
CPC .............. *A61F 2/9661* (2020.05); *A61F 2/07* (2013.01); *A61F 2/2436* (2013.01); (Continued)

(58) Field of Classification Search
CPC ........ A61F 2/9661; A61F 2/07; A61F 2/2436; A61F 2/9517; A61F 2/954; A61F 2002/9505; A61F 2002/9665
See application file for complete search history.

(56) References Cited

U.S. PATENT DOCUMENTS 6,773,457 B2 8/2004 Ivancev et al.
8,052,732 B2 11/2011 Mitchell et al.
(Continued)

FOREIGN PATENT DOCUMENTS

CN 104394799 A 3/2015
CN 106659576 A 5/2017
(Continued)

OTHER PUBLICATIONS

First Office Action, CN Application No. 201980023276.2, mailed Jan. 22, 2024.

(Continued)

*Primary Examiner* — Thomas C Barrett
*Assistant Examiner* — Mikail A Mannan
(74) *Attorney, Agent, or Firm* — Medler Ferro Woodhouse & Mills PLLC

(57) ABSTRACT

A delivery catheter includes a tip, a spindle and a lock mechanism. The tip includes a tapered portion and a tip sleeve. The tip sleeve extends proximally and has a lumen. The spindle includes a plurality of spindle pins. The lock mechanism locks the tip sleeve to the spindle to prevent relative longitudinal movement between the spindle and the tip sleeve. The delivery catheter includes a delivery configuration with the tip sleeve covering the spindle pins and a release configuration with a proximal end of the tip sleeve distal of the spindle pins. The lock mechanism locks the prosthesis delivery system in the release configuration. Each spindle pin of the plurality of spindle pins includes a smooth, curved profile.

11 Claims, 24 Drawing Sheets

(51) Int. Cl.

| | |
|---|---|
| ***A61F 2/24*** | (2006.01) |
| ***A61F 2/95*** | (2013.01) |
| ***A61F 2/954*** | (2013.01) |

(52) U.S. Cl.

CPC ..... *A61F 2002/9505* (2013.01); *A61F 2/9517* (2020.05); *A61F 2/954* (2013.01); *A61F 2002/9665* (2013.01)

(56) References Cited

U.S. PATENT DOCUMENTS

| | | | | |
|---|---|---|---|---|
| 8,740,963 | B2 | 6/2014 | Arbefeuille et al. | |
| 8,764,811 | B2 | 7/2014 | Rea Peterson et al. | |
| 8,882,828 | B2 | 11/2014 | Kinkade et al. | |
| 9,775,706 | B2 | 10/2017 | Peterson et al. | |
| 9,925,031 | B2 | 3/2018 | Macatangay | |
| 11,123,208 | B2 * | 9/2021 | Murray, III | A61F 2/9661 |
| 2004/0093063 | A1 * | 5/2004 | Wright | A61F 2/95 623/1.12 |
| 2011/0251665 | A1 | 10/2011 | Schmitt et al. | |
| 2011/0257720 | A1 | 10/2011 | Peterson et al. | |
| 2015/0272759 | A1 * | 10/2015 | Argentine | A61F 2/966 623/1.11 |
| 2017/0340462 | A1 | 11/2017 | Lostetter | |

FOREIGN PATENT DOCUMENTS

| | | | |
|---|---|---|---|
| WO | 2010/0045297 | A2 | 4/2010 |
| WO | 2013162685 | A1 | 10/2013 |
| WO | 2016025807 | A1 | 2/2016 |

OTHER PUBLICATIONS

PCT/US2019/022724, The International Search Report and Written Opinion, mailed Jun. 19, 2019, 14pgs.

* cited by examiner 102
108
152
155
148
114
154
152
144

102
108
149
148
118
182
152
153
180
144
114
LAs 1100
1112
1144
1114
1108
1197
1116
201
1110
1106
1102
1196
223
221
1104

1118
1197
1144
1198
1196
1114
1197
1198

PROSTHESIS DELIVERY SYSTEM WITH TIP TRAVEL LIMITER AND METHOD OF USE

RELATED APPLICATIONS

This application is a Continuation of and claims the benefit of U.S. patent application Ser. No. 15/939,353 filed Mar. 29, 2018, now allowed. The disclosures of which are herein incorporated by reference in their entirety.

FIELD OF THE INVENTION

The present invention relates to systems and methods for intravascular delivery and deployment of a stent-graft prosthesis. More particularly, the present invention relates to a prosthesis delivery system in which the travel of a tip of the prosthesis delivery system is limited.

BACKGROUND OF THE INVENTION

The wall of an aorta is generally elastic and stretches and shrinks to adapt to blood flow. However, with age, and some medical conditions such as high blood pressure and/or atherosclerosis, the wall of the aorta may be weakened. Pressure on the weakened section of the aorta may overstretch and bulge, forming an aortic aneurysm. Aortic aneurysms may burst, causing serious bleeding and/or death. While aortic aneurysms may form in any section of the aorta, they are most common in the abdominal region. Aneurysms in the abdominal region are known as abdominal aortic aneurysms, or AAA.

The treatment of an aortic aneurysm depends both on the location of the aneurysm and its size. Treatment options may include surgery and/or medication. Traditional open surgery inflicts significant patient trauma, requires extensive recovery times and may result in life-threatening complications. Medication treatment may not be sufficient in many cases.

Rather than performing an open surgical endovascular procedure, efforts have been made to perform aneurysm repair using minimally invasive techniques including percutaneous transcatheter (transluminal) delivery and deployment, release, or implantation of a stent-graft prosthesis at a treatment site. A stent-graft prosthesis is a stent or stents coupled to a graft material. More particularly, a lumen or vasculature is accessed percutaneously at a convenient and less traumatic entry point, and the stent-graft prosthesis is routed through the vasculature to the site where the stent-graft prosthesis is to be deployed. Intraluminal deployment is typically effected using a delivery catheter with coaxial inner and outer tubes or shafts arranged for relative axial movement. For example, a self-expanding stent-graft prosthesis may be compressed and disposed within a distal end of an outer shaft or sheath component of the delivery catheter distal of a stop fixed to an inner shaft or member. The delivery catheter is then maneuvered, typically tracked through a body lumen until a distal end of the delivery catheter and the stent-graft prosthesis are positioned at the intended treatment site. The stop on the inner shaft is then held stationary while the outer sheath component of the delivery catheter is withdrawn. The stop on the inner shaft prevents the stent-graft prosthesis from being withdrawn with the outer sheath. As the outer sheath is withdrawn, the stent-graft prosthesis is released from the confines thereof and radially self-expands so that at least a portion of it contacts and substantially conforms to a portion of the surrounding interior of the lumen, e.g., the blood vessel wall or anatomical conduit. When fully released, the stent-graft prosthesis extends both distal and proximal of the aneurysm and forms a new passageway within the vasculature, thereby reducing pressure on the weakened wall of the aneurysm.

In recent years, to improve optimal control and alignment during deployment and positioning of a stent-graft prosthesis, various tip capture mechanisms have been incorporated into the delivery system utilized for percutaneously delivering the stent-graft prosthesis. Tip capture involves restraining a proximal end stent of the stent-graft prosthesis in conjunction with a main body restraint achieved by other delivery system components, such as a tubular outer shaft or sheath. The tip capture mechanism can be activated at any time during stent-graft prosthesis deployment to suit any number of system characteristics driven by the therapy type, stent-graft type, or specific anatomical conditions that may prescribe the release timing. Typically, the tip capture release is activated after some or all of the main stent-graft prosthesis body release, and thus provides a means of restraining the stent-graft prosthesis during positioning. Additional restraint of the stent-graft prosthesis is a key characteristic when the operator is attempting to accurately position the stent-graft prosthesis relative to an anatomical target, such as an aneurysm.

For example, U.S. Pat. No. 8,052,732 to Mitchell et al., which is herein incorporated by reference in its entirety describes tip capture mechanisms that restrain a proximal end stent of the stent-graft prosthesis while the remainder of the stent-graft prosthesis expands, then releases the proximal end stent. The proximal end stent is attached to the graft material of the stent-graft prosthesis so as to have an "open web" or "free flow" proximal end configuration in which the endmost crowns thereof extend past or beyond the graft material such that the endmost crowns are exposed or bare, and thus free to interact with a tip capture mechanism and couple the prosthesis to the delivery system.

However, attendant with the percutaneous delivery and release of a stent-graft prosthesis at a treatment location, the distal portion of the delivery catheter must be retracted through the deployed stent-graft prosthesis for removal from the patient. With current delivery catheter designs, a gap forms between components of the tip capture mechanism of the delivery catheter as the stent-graft prosthesis is deployed. This gap may comprise multiple edges that may snag, catch, tear, or otherwise damage the deployed stent-graft prosthesis or anatomy as the distal portion of the delivery catheter is withdrawn through the deployed stent-graft prosthesis.

Accordingly, there is a need for improved delivery catheter designs and methods that improve the release of the stent-graft prosthesis, improve the ease with which a distal portion of the delivery catheter may be removed, and minimize the potential of the delivery catheter to damage the deployed stent-graft prosthesis or anatomy during the removal of the distal portion of the delivery catheter.

BRIEF SUMMARY OF THE INVENTION

Embodiments hereof are directed to a delivery catheter including a tip, a spindle, and a lock mechanism. The tip includes a tapered portion and a tip sleeve. The tip sleeve extends proximally and has a lumen. The spindle includes a plurality of spindle pins. The lock mechanism locks the tip sleeve to the spindle, thereby preventing relative longitudinal movement between the tip sleeve and the spindle.

Embodiments hereof are also directed to a prosthesis delivery system including a stent-graft prosthesis and a delivery catheter. The stent-graft prosthesis includes a proximal bare stent, at least one stent ring distal of the proximal bare stent and a graft material. The stent-graft prosthesis has a radially compressed configuration for delivery within a vasculature and a radially expanded configuration for deployment. The delivery catheter has a delivery configuration and a release configuration. The delivery catheter includes a tip, a spindle, a lock mechanism, and an outer sheath. The tip includes a tapered portion and a tip sleeve extending proximally. The tip sleeve is configured to retain a proximal portion of the stent-graft prosthesis in a radially compressed state for delivery to a treatment location. The spindle includes a plurality of spindle pins. The lock mechanism is configured to lock the tip sleeve to the spindle to prevent relative longitudinal movement between the spindle and the tip sleeve when the delivery catheter is in the release configuration. The outer sheath is configured to retain a distal portion of the stent-graft prosthesis in a radially compressed state for delivery to a treatment location.

Embodiments hereof are further related to a method of delivering and releasing a stent-graft prosthesis. The method includes loading a stent-graft prosthesis onto a delivery catheter. The delivery catheter includes an outer sheath, a spindle, an inner shaft, a tip and a lock mechanism. The tip includes tapered portion and a tip sleeve. The delivery catheter is positioned at a desired treatment location within a vessel. Once positioned at the desired treatment location, the outer sheath is retracted and a first portion of the stent-graft prosthesis returns to an expanded state. With the first portion of the stent-graft prosthesis in the expanded state, the inner shaft of the delivery catheter is advanced distally and a second portion of the stent-graft prosthesis returns to an expanded state. Further, the inner shaft is advanced distally to engage the lock mechanism and lock the tip sleeve to the spindle.

BRIEF DESCRIPTION OF DRAWINGS

The foregoing and other features and advantages of the invention will be apparent from the following description of embodiments thereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION OF THE INVENTION

Specific embodiments of the present invention are now described with reference to the figures, wherein like reference numbers indicate identical or functionally similar elements. The terms "distal" and "proximal", when used in the following description to refer to a delivery system, a delivery catheter, or delivery components are with respect to a position or direction relative to the treating clinician. Thus, "distal" and "distally" refer to positions distant from or in a direction away from the treating clinician, and the terms "proximal" and "proximally" refer to positions near or in a direction toward the treating clinician. The terms "distal" and "proximal", when used in the following description to refer to a native vessel, native valve, or a device to be implanted into a native vessel or native valve, such as a stent-graft prosthesis, are with reference to the direction of blood flow. Thus, "distal" and "distally" refer to positions in a downstream direction with respect to the direction of blood flow and the terms "proximal" and "proximally" refer to positions in an upstream direction with respect to the direction of blood flow.

The following detailed description is merely exemplary in nature and is not intended to limit the invention or the application and uses of the invention. Although the description of embodiments hereof is in the context of the treatment of blood vessels such as the aorta, the invention may also be used in any other body passageways where it is deemed useful. Furthermore, there is no intention to be bound by any expressed or implied theory presented in the preceding technical field, background, brief summary or the following detailed description.

Figure 1:
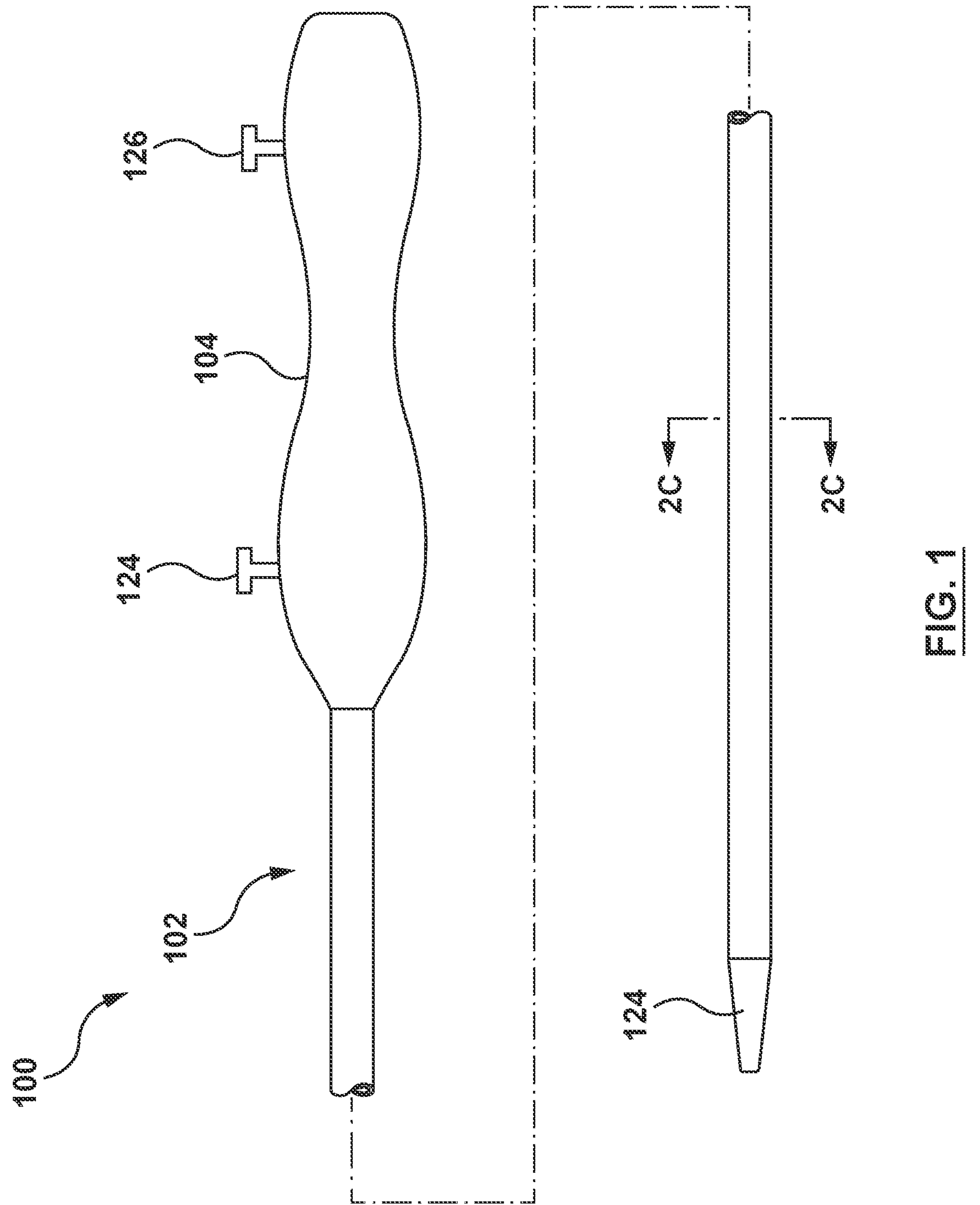
FIG. 1 depicts a side view of a prosthesis delivery system in accordance with an embodiment hereof.
Figure 2:
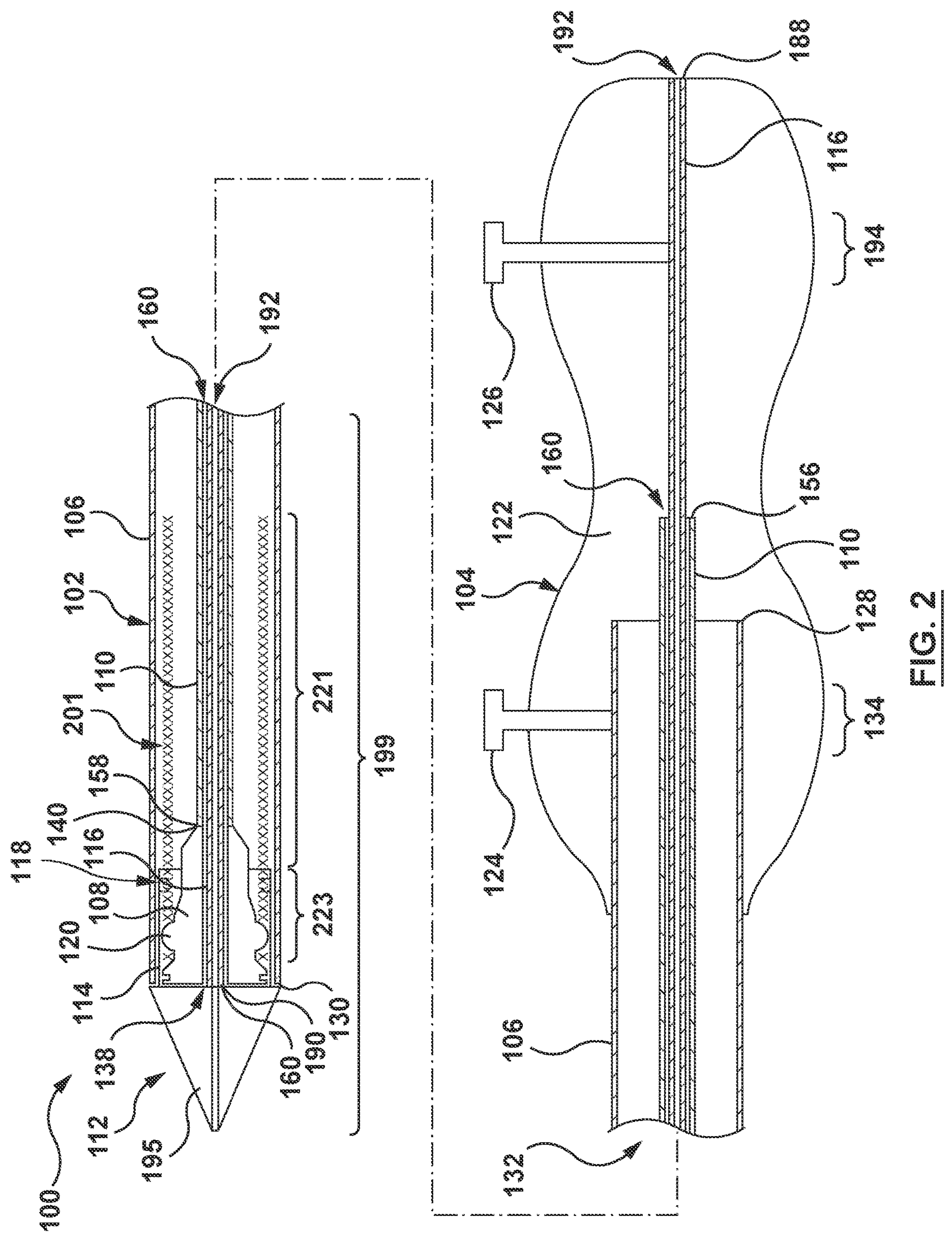
FIG. 2 depicts a longitudinal cross-sectional view of the prosthesis delivery system of FIG. 1, wherein a delivery catheter of the prosthesis delivery system is in a delivery configuration and a stent-graft prosthesis is in a radially compressed configuration.
Figure 2A:
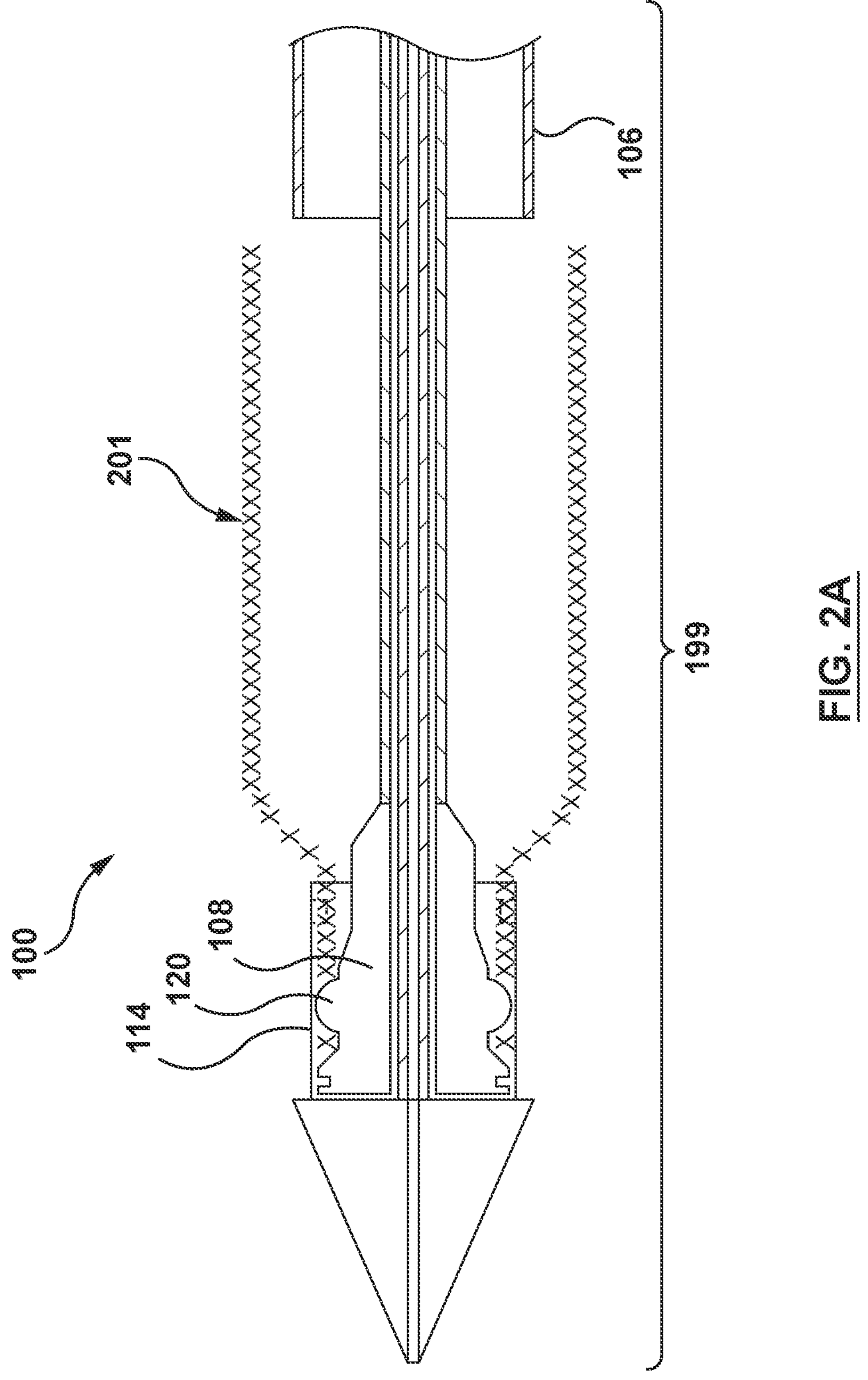
FIG. 2A depicts a longitudinal cross-sectional view of a distal portion of the prosthesis delivery system of FIG. 1, wherein the delivery catheter is in a partial release configuration.
Figure 2B:
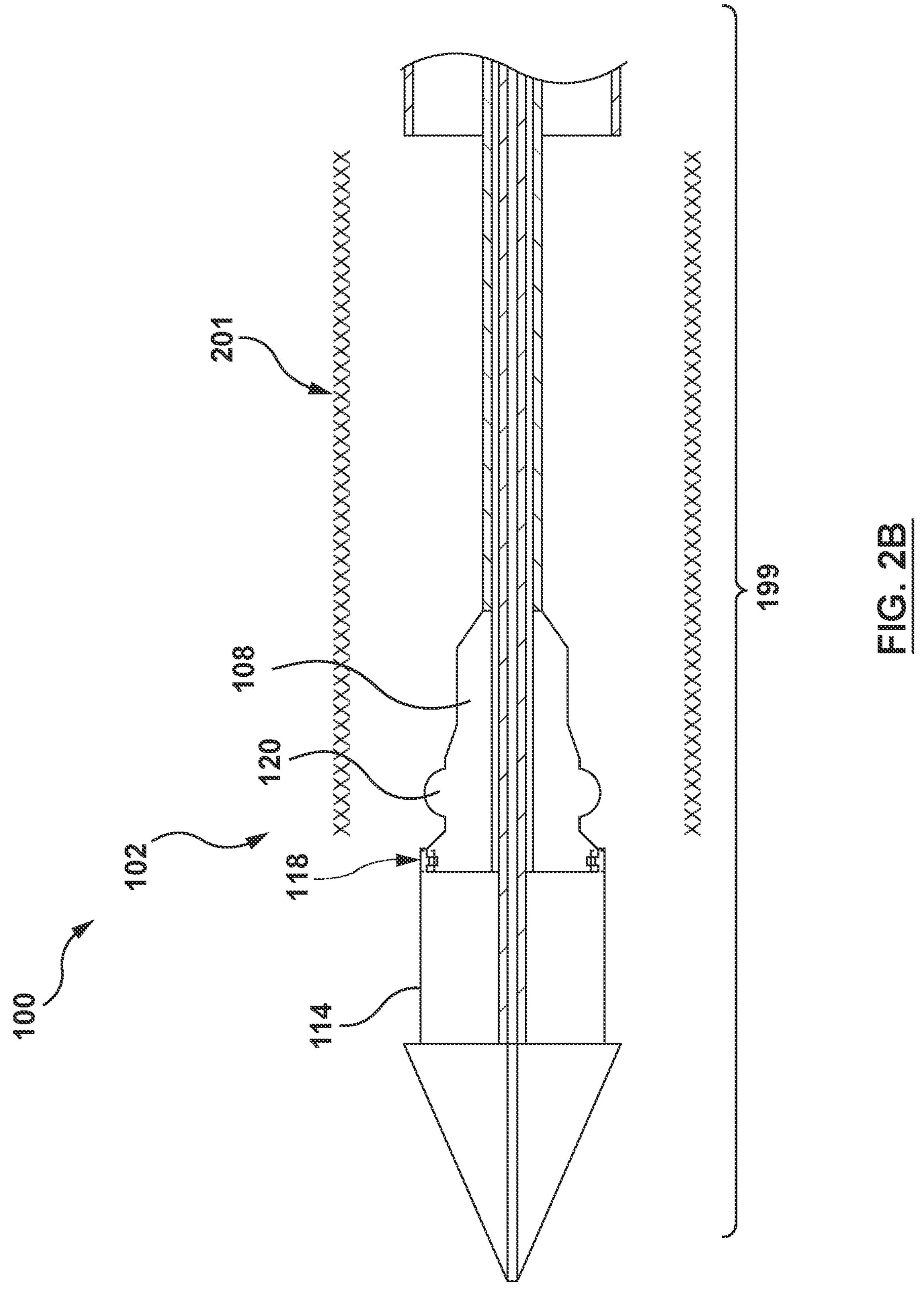
FIG. 2B depicts a longitudinal cross-sectional view of the distal portion of the prosthesis delivery system of FIG. 1, wherein the delivery catheter is in the release configuration.
Figure 2C:
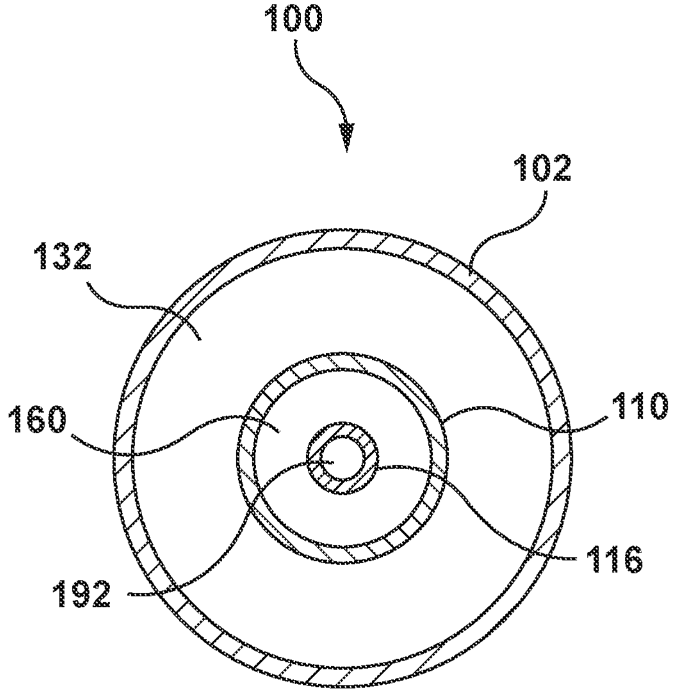
FIG. 2C depicts a cross-sectional view of the prosthesis delivery system taken at line 2C-2C of FIG. 1.

FIGS. 1-10 illustrates a prosthesis delivery system 100 in accordance with an embodiment hereof. The prosthesis delivery system 100 includes a delivery catheter 102, also referred to herein as a delivery device, and a stent-graft prosthesis 201 mounted in a radially compressed configuration at a distal portion 199 of the delivery catheter 102, as shown in FIGS. 1-2. FIG. 1 is a side view of the prosthesis delivery system 100, FIG. 2C is cross-section of the prosthesis delivery system 100 taken at line 2C-2C of FIG. 1, and FIG. 2 is a sectional view of the prosthesis delivery system 100. The prosthesis delivery system 100 is configured to deliver and release or deploy the stent-graft prosthesis 201 at a desired treatment location. Accordingly, the prosthesis delivery system 100 is sized and configured to be advanced through a vasculature in a minimally invasive manner. An introducer sheath (not shown) or a guide catheter (not shown) may be used with the delivery catheter 102 to minimize intravascular trauma during introduction, tracking and delivery of the delivery catheter 102 to the desired treatment location.

Figure 3:
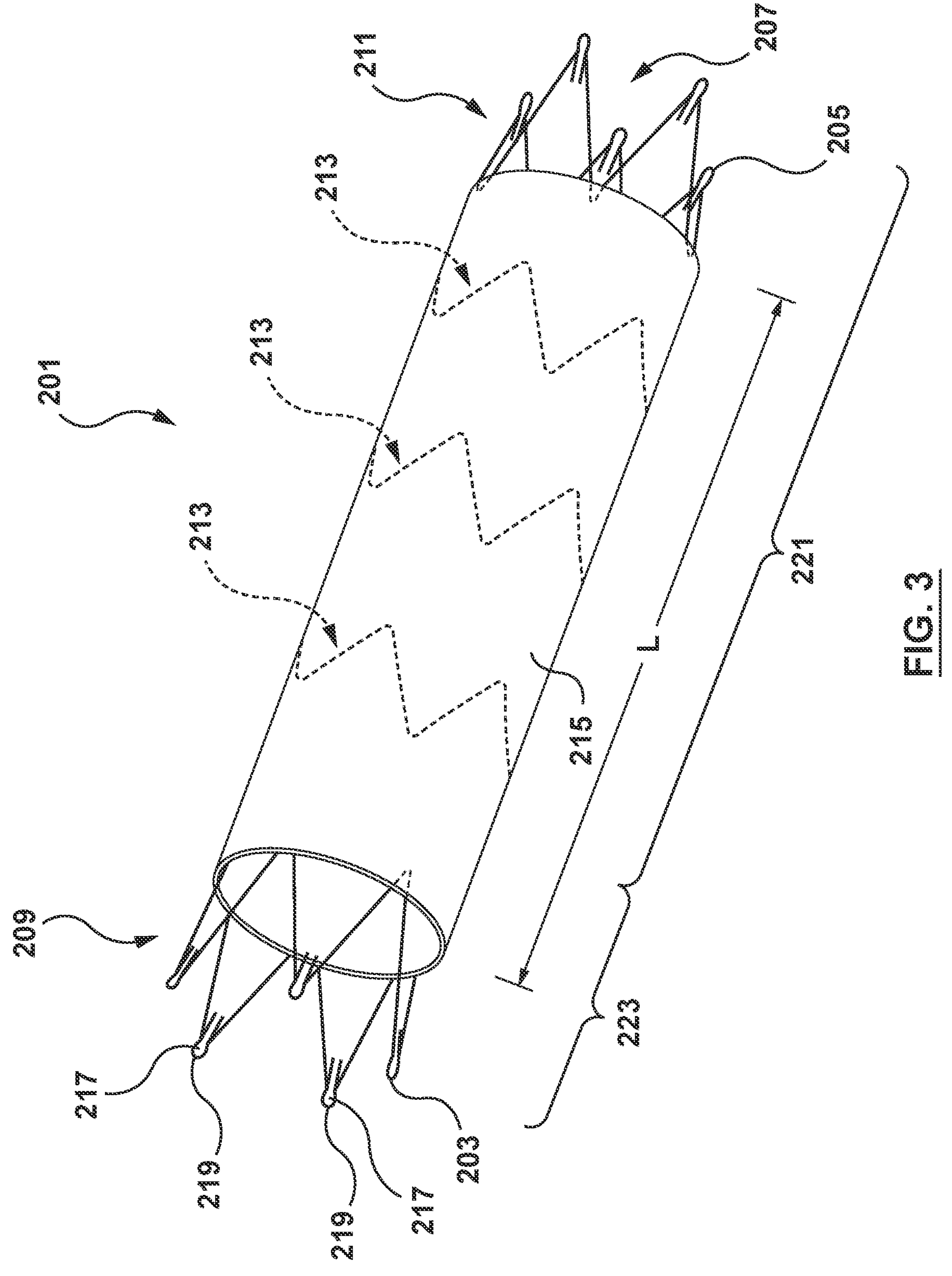
FIG. 3 depicts a perspective view of an exemplary stent-graft prosthesis suitable for use with the prosthesis delivery system of FIG. 1.

FIG. 3 shows an exemplary embodiment of the stent-graft prosthesis 201 suitable for use with the prosthesis delivery system 100. The stent-graft prosthesis 201 includes a proximal end 203, a distal end 205, and a lumen 207 extending from the proximal end 203 to the distal end 205. The stent-graft prosthesis 201 further includes a proximal bare or anchor stent 209, a distal bare or anchor stent 211, a plurality of stent rings 213 and a graft material 215. While described herein with the proximal bare stent 209, the distal bare stent 211, and the plurality of stent rings 213, the stent-graft prosthesis 201 may alternatively be formed from unitary laser cut tube, or any other suitable scaffold or stent structure. The stent-graft prosthesis 201 includes a radially compressed configuration for delivery and a radially expanded configuration when deployed. When the stent-graft prosthesis 201 is in the radially expanded configuration at a desired treatment location, the stent-graft prosthesis 201 is configured to repair an aneurysm within a vessel.

The proximal bare stent 209 is a stent ring configured to anchor the proximal end 203 of the stent-graft prosthesis 201 to the wall of a vessel when the stent-graft prosthesis 201 is in the radially expanded configuration. The proximal bare stent 209 includes a plurality of openings 217 defined by proximal apexes 219 of the proximal bare stent 209. As will be explained in more detail herein, each of the plurality of openings 217 is configured to receive a corresponding spindle pin 120 (visible in FIG. 4) of a spindle 108 (visible in FIG. 4) when the stent-graft prosthesis 201 is in the radially compressed configuration and loaded on the delivery catheter 102 (visible in FIG. 1). A distal portion of the proximal bare stent 209 is coupled to a proximal portion of the graft material 215.

Similarly, the distal bare stent 211 is a stent ring configured to anchor the distal end 205 of the stent-graft prosthesis 201 to the wall of the vessel when the stent-graft prosthesis 201 is in the radially expanded configuration. A proximal portion of the distal bare stent 211 is coupled to a distal portion of the graft material 215. While the stent-graft prosthesis 201 is described herein with the distal bare stent 211, in an alternative embodiment, the distal bare stent 211 may be omitted from the stent-graft prosthesis 201.

The plurality of stent rings 213 are configured to support the graft material 215 when the stent-graft prosthesis 201 is in the radially expanded configuration. In other words, the plurality of stent rings 213 hold the lumen 207 of the stent-graft prosthesis 201 open when the stent-graft prosthesis 201 is in the radially expanded configuration. Each stent ring 213 is coupled to an inner surface of the graft material 215, although it will be understood by one of ordinary skill in the art that stent rings 213 may alternatively be coupled to an outer surface of the graft material.

In embodiments hereof, the proximal and distal bare stents 209, 211, and each of the plurality of support stents 213 is self-expanding to return to a radially expanded state from a radially compressed state. The proximal and distal bare stents 209, 211, and each of the plurality of support stents 213 may be formed of various materials including, but not limited to stainless steel, nickel-titanium alloys (e.g. NITINOL), or other suitable materials. "Self-expanding" as used herein means that a structure has a mechanical memory to return to the radially expanded configuration. The proximal and distal bare stents 209, 211, and each of the plurality of support stents 213 may be coupled to the graft material 215 by method such as, but not limited to sutures, adhesives, or other methods suitable for the purposes described herein.

As shown in FIG. 3, the graft material 215 is of a generally tubular shape. The graft material 215 has a longitudinal length L, which may vary based upon the application. The graft material 215 may be formed from any suitable graft material, for example and not limited to, a low-porosity woven or knit polyester, DACRON material, expanded polytetrafluoroethylene, polyurethane, silicone, or other suitable materials. In another embodiment, the graft material could also be a natural material such as pericardium or another membranous tissue such as intestinal submucosa.

The stent-graft prosthesis 201 is deployed at the site of an aneurysm such that the stent-graft prosthesis 201 spans the aneurysm. More specifically, when the stent-graft prosthesis 201 is in the radially expanded configuration at the site of an aneurysm, the proximal bare stent 209 is disposed proximal of the aneurysm and anchors the proximal end 203 of the stent-graft prosthesis 201 to healthy tissue proximal of the aneurysm. Similarly, the distal bare stent 211 is disposed distal of the aneurysm and anchors the distal end 205 of the stent-graft prosthesis 201 to healthy tissue distal of the aneurysm when the stent-graft prosthesis 201 is in the radially expanded configuration at the site of an aneurysm. The graft material 215 spans the aneurysm and the lumen 207 provides a conduit for blood flow through the vessel, thereby reducing pressure on the aneurysm.

The stent-graft prosthesis 201 is described and illustrated herein to facilitate description of the systems, devices and methods to deliver and release a stent-graft prosthesis according to embodiments hereof. It is understood that the stent-graft prosthesis 201 is merely exemplary and any number of alternate stent-graft prostheses can be used with the systems, devices and methods described herein. For example, and not by way of limitation, the number of apexes of the proximal bare stent 209, the distal bare stent 211, and each of the ring stents 213 may be greater or less than shown in FIG. 3. Further, while shown with three (3) stent rings, the stent-graft prosthesis 201 may include more or fewer stent rings 213 as required by the application.

As shown in FIG. 2, the delivery catheter 102 includes a handle 104, an outer sheath 106, a spindle 108, a spindle shaft 110, a tip 112 including a tapered distal portion 195 and a tip sleeve 114, an inner shaft 116, and a lock mechanism 118. The delivery catheter 102 is configured to retain the stent-graft prosthesis 201 in a radially compressed configuration for delivery to the desired treatment location. The delivery catheter 102 includes a delivery configuration shown in FIG. 2 in which the tip sleeve 114 covers a plurality of spindle pins 120 of the spindle 108 and the outer sheath 106 covers the spindle 108, a partial release configuration shown in FIG. 2A in which the tip sleeve 114 covers the plurality of spindle pins 120 and the outer sheath 106 has been retracted such that the outer sheath 106 does not cover the spindle 108, and a release configuration shown in FIG. 2B in which tip sleeve 114 has been advanced such that a proximal end of the tip sleeve 114 is distal of the plurality of spindle pins 120 and the lock mechanism 118 locks the delivery catheter 102 in the release configuration.

The handle 104 includes a housing 122, a first actuating mechanism 124 and a second actuating mechanism 126, as shown in FIG. 2. The handle 104 is configured with the first and the second actuating mechanisms 124, 126 each extending through the housing 122 for interfacing by a user. The first actuating mechanism 124 is configured to retract or pull the outer sheath 106 proximally with respect to the spindle shaft 110. The second actuating mechanism 126 is configured to push or advance the inner shaft 116 distally with respect to the spindle shaft 110 such that the tip 112, including the tip sleeve 114, move distally relative to the spindle 108. The handle 104 provides a surface for convenient handling and grasping by a user, and can have a variety of shapes, including, but not limited to a cylindrical shape. While the handle 104 is shown with a specific style of first and second actuating mechanisms 124, 126, this is not meant to limit the design, and various actuating mechanisms may be utilized such as, but not limited to axially-slidable levers, rotary rack and pinion gears, or other applicable actuating mechanisms.

As best shown in the cross-sectional view of FIG. 2C, the delivery catheter 102 includes the outer sheath 106, the spindle shaft 110, and the inner shaft 116 concentrically disposed about each other. More specifically, the spindle shaft 110 is concentrically disposed about the inner shaft 116, and the outer sheath 106 is concentrically disposed about the spindle shaft 110.

As best shown in FIG. 2, the outer sheath 106 includes a proximal end 128, a distal end 130, and a lumen 132. The lumen 132 extends from the proximal end 128 to the distal end 130 of the outer sheath 106 and is sized to receive the spindle shaft 110, the spindle 108 and the tip sleeve 114. A distal portion of the outer sheath 106 is configured to retain a first portion 221 of the stent-graft prosthesis 201 in a radially compressed state for delivery to the desired treatment location. The first portion 221 of the stent-graft prosthesis 201, as used herein, means that portion of the stent-graft prosthesis 201 disposed over the spindle shaft 110 and the spindle 108 but not encapsulated by the tip sheath 114 when the prosthesis delivery system 100 is in the delivery configuration of FIG. 2. A second portion 223 of the stent-graft prosthesis 201, as used herein, means that portion of the stent-graft prosthesis 201 disposed over the spindle 108 and held in a radially compressed state by the tip sheath 114 when the prosthesis delivery system 100 is in the delivery configuration of FIG. 2. The proximal end 128 of the outer sheath 106 is configured for fixed connection to the handle 104. More particularly, the proximal end 128 extends proximally into the housing 122 of the handle 104 and a proximal portion 134 of the outer sheath 106 is rigidly connected to the first actuating mechanism 124 of the handle 104. The proximal portion 134 is coupled to the first actuating mechanism 124 such that movement of the first actuating mechanism 124 causes the outer sheath 106 to move relative to the spindle shaft 110, the spindle 108, the inner shaft 116, the tip 112, and the handle 104.

The spindle shaft 110 includes a proximal end 156, a distal end 158, and a lumen 160. The lumen 160 extends from the proximal end 156 to the distal end 158 of the spindle shaft 110. The lumen 160 is sized to receive the inner shaft 116 such that the inner shaft 116 is longitudinally slidable relative to the spindle shaft 110 when the delivery catheter 102 is in the delivery configuration. The distal end 158 of the spindle shaft 110 is attached to a proximal end 140 of the spindle 108 such that the lumen 160 of the spindle shaft is longitudinally aligned with the lumen 138 of the spindle 108, forming a continuous lumen from the proximal end 156 of the spindle shaft 110 to the distal end 142 of the spindle 108. The proximal end 156 of the spindle shaft 110 is configured for fixed connection to the handle 104. The spindle shaft 110 may be coupled to the spindle 108 for example, and not by way of limitation by adhesives, welding, clamping, and other coupling methods.

Referring again to FIG. 2, the inner shaft 116 is a substantially hollow body including a proximal end 188, a distal end 190 and a lumen 192. The lumen 192 extends from the proximal end 188 to the distal end 190 and is sized to slidably receive auxiliary devices (e.g. a guidewire). The distal end 190 of the inner shaft 116 is attached to the proximal end 162 of the tapered portion 195 of the tip 112 and the inner shaft 116 extends proximally through the spindle 108 and the spindle shaft 110 to at least the second actuating mechanism 126. More precisely, the inner shaft 116 extends proximally through the housing 122 of the handle 104 and a proximal portion 194 of the inner shaft 116 is rigidly connected to the second actuating mechanism 126 of the handle 104. The proximal portion 194 is coupled to the second actuating mechanism 126 such that movement of the second actuating mechanism 126 causes the inner shaft 116, the tip 112, including the tip sleeve 114, to move relative to the spindle shaft 110, the spindle 108, the outer sheath 106 and the handle 104. While the inner shaft 116 is described herein as single component, this is not meant to be limiting, and the inner shaft 116 may include components such as, but not limited to a proximal shaft, a distal shaft, or other components. The tip 112 may be coupled to the inner shaft 116, for example, and not by way of limitation by adhesives, welding, clamping, and other coupling devices as appropriate.

The outer shaft 106, the spindle shaft 110, and the inner shaft 116 may each be constructed of materials such as, but not limited to polyurethane, polyether block amide (PEBA), polyamide polyether block copolymer, polyethylene, or other materials suitable for the purposes of the present disclosure. The proximal portion 134 of the outer sheath 106, the proximal end 156 of the spindle shaft 110, and the proximal portion 194 of the inner shaft 116 may be coupled to the first actuating mechanism 124, the handle 104, and the second actuating mechanism 126, respectively, for example, and not by way of limitation by adhesives, welding, clamping, and other coupling devices as appropriate.

Figure 4:
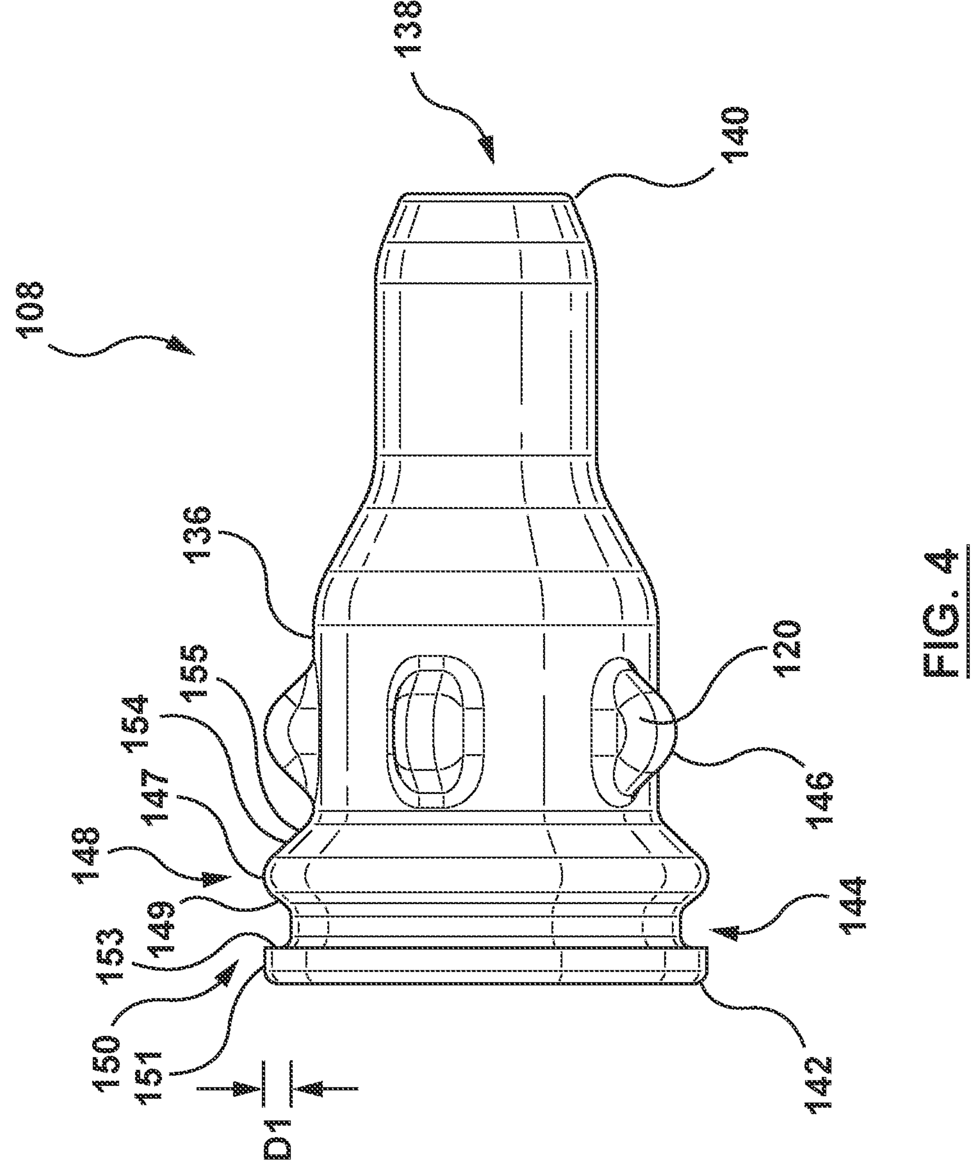
FIG. 4 depicts a side view of a spindle of the delivery catheter of FIG. 2.

As previously described, the spindle 108 is disposed at the distal end 158 of the spindle shaft 110. FIG. 4 illustrates a side view of the spindle 108 removed from the prosthesis delivery system 100 for illustrative purposes only. As shown in FIG. 4, the spindle 108 includes a generally tubular body 136, a lumen 138 extending from the proximal end 140 to a distal end 142, a plurality of spindle pins 120, and a radial groove 144 defined by a proximal wall 148 and a distal wall 150. The term "generally" or "substantially" as used herein, particularly with respect to the terms "cylindrical", "flat", and "tubular" means within normal manufacturing tolerances. The spindle 108 is configured to be slidably disposed within the tip sleeve 114 of the tip 112 such that the tip sleeve 114 may move relative to the spindle 108. The lumen 138 is configured to slidably receive the inner shaft 116.

The proximal wall 148 of the spindle 108 includes an outer shoulder 154, a crown 147, and an inner shoulder 149. The outer shoulder 154 of the proximal wall 148 includes a smooth, angled or tapered outer surface 155. The outer surface 155 is configured to ease the release of the stent-graft prosthesis 201 as the delivery catheter 102 transitions from the delivery configuration to the release configuration. More precisely, the outer surface 155 of the proximal wall 154 makes expansion of the stent-graft prosthesis 201 from the radially compressed configuration to the radially expanded configuration easier as the frictional forces between the expanding stent-graft prosthesis 201 and the outer surface 155 of the proximal wall 149 are reduced by the tapered or angled profile of the outer surface 155. Further, the stent-graft-prosthesis 201 will not catch or otherwise hang-up on the outer surface 155 as the stent-graft prosthesis 201 radially expands. The outer surface 155 of the outer shoulder 154 is further configured to create a tapered transition from the spindle 108 to the tip sheath 114 when the delivery catheter 102 is in the release configuration such that the stent-graft prosthesis 201 may not catch or otherwise snag on the transition between the spindle 108 and the tip sheath 114 as the delivery catheter 102 is proximally retracted through the deployed stent-graft prosthesis 201. The crown 147 of the proximal wall 148 is substantially flat such that when the delivery catheter 102 is in the release configuration, the transition between the spindle 108 and the tip sheath 114 is minimized. The term "flat" as used herein means that the surface is planar and oriented parallel to a longitudinal axis of the spindle 108. The term "minimized" as used herein means that the distance between the adjacent surfaces of two components is reduced to the smallest possible amount or degree. Thus, minimization of the transition between the spindle 108 and the tip sheath 114 reduces the possibility that the stent-graft prosthesis 201 may catch or otherwise snag on the spindle 108 and/or the tip sheath 114 as the delivery catheter 102 is proximally retracted through the deployed stent-graft prosthesis 201. Accordingly, the configuration of the spindle 108 eases the removal of the distal portion 199 of the delivery catheter 102 from within the stent-graft prosthesis 201. The distal wall 150 includes a crown 151 and an inner shoulder 153. Non-limiting examples of materials suitable for the construction of the spindle 108 include polyurethane, polyether block amide (PEBA), polyamide polyether block copolymer, polyethylene, or other materials suitable for the purposes of the present disclosure.

The plurality of spindle pins 120 are circumferentially spaced around the body 136 of the spindle 108. Each spindle pin 120 extends radially outward from the body 136 of the spindle 108 such that an outer profile 146 of each spindle pin 120 is disposed adjacent to an inner surface of the tip sleeve 114 when the delivery catheter 102 is in the delivery configuration. The plurality of spindle pins 120 of the spindle 108 are configured to maintain the longitudinal position of the stent-graft prosthesis 201 in relation to the spindle 108 of the delivery catheter 102 as the delivery catheter 102 transitions from the delivery configuration to the release configuration.

Each spindle pin 120 is a raised bump or protrusion including a smooth, curved outer surface or profile 146. The outer profile 146 is configured to ease the release of the stent-graft prosthesis 201 from the delivery catheter 102. More specifically, the outer profile 146 makes expansion of the stent-graft prosthesis 201 from the radially compressed configuration to the radially expanded configuration easier as the frictional forces between the expanding stent-graft prosthesis 201 and the outer profile 146 of each spindle pin 120 is reduced by the curved profile of the outer profile 146. Further, the stent-graft-prosthesis 201 will not catch or otherwise hang-up on the outer profile 146 as the stent-graft prosthesis 201 radially expands. The smooth, curved outer profile 146 is further configured to enable snag-free/catch-free removal of the spindle 108 from the deployed stent-graft prosthesis 201, as described below. While illustrated in FIG. 4 with a specific number of spindle pins 120, this is not meant to be limiting, and more or fewer spindle pins 120 may be utilized.

The radial groove 144 is defined between the proximal wall 148 and the distal wall 150 at a distal portion of the spindle 108. As will be described in more detail herein with respect to FIG. 8, the radial groove 144 is configured to retain a plurality of tabs 152 (visible in FIG. 5) of the tip sleeve 114 (visible in FIG. 5), when the delivery catheter 102 (visible in FIG. 5) is in the release configuration. The radial groove 144 is formed with a sufficient depth D1 optimized such that each tab 152 (visible in FIG. 4), once extended within the radial groove 144 may not exit or leave the radial groove 144.

Figure 5:
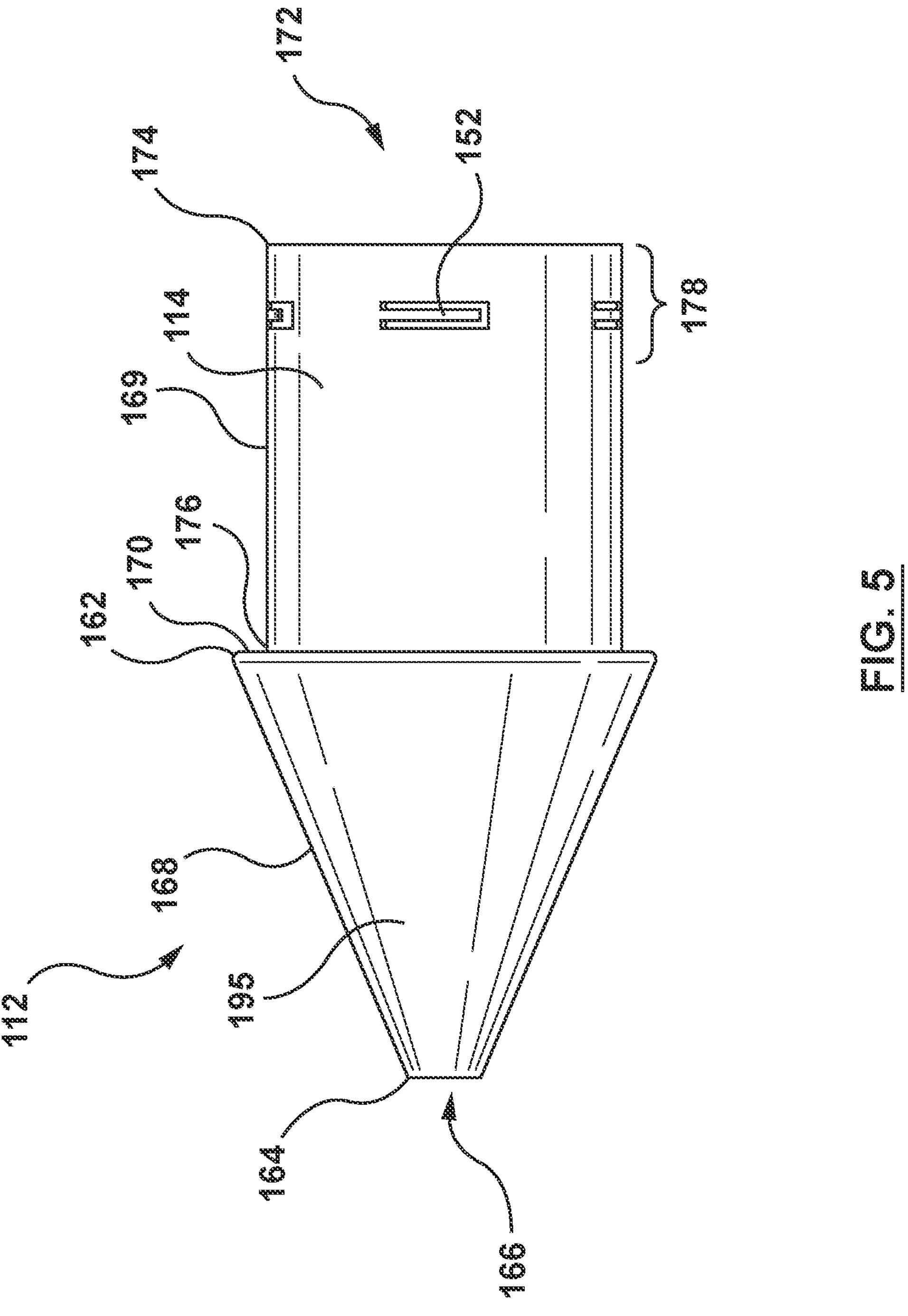
FIG. 5 depicts a side view of a tip of the delivery catheter of FIG. 2.

As previously stated, the tip 112 is disposed at the distal end 190 of the inner shaft 116. FIG. 5 illustrates a side view of the tip 112 removed from the prosthesis delivery system 100 for illustrative purposes only. The tip 112 includes the generally conical tapered portion 195 disposed at a distal portion thereof, and the tip sleeve 114 disposed at a proximal portion thereof. The tip 112 and it components may be constructed of materials such as, but not limited to polyurethane, polyether block amide (PEBA), polyamide polyether block copolymer, polyethylene, or other suitable materials.

The tapered portion 195 includes a proximal end 162, a distal end 164, and a lumen 166 extending from the proximal end 162 to the distal end 164. The distal end 164 of the tapered portion is also the distal end of the tip 112. An outer surface 168 of the tapered portion 195 extends proximally from the distal end 164 and gradually increases diameter to the proximal end 162, forming the generally conical shape. The tapered portion 195 further includes a circumferential shoulder 170 at the proximal end 162 extending radially inward from the outer surface 168 to an outer surface 169 of the tip sheath 114.

The tip sleeve 114 is a generally cylindrical tube extending proximally from the proximal end 162 of the tapered portion 195. The tip sleeve 114 includes a lumen 172 extending from a proximal end 174 to a distal end 176 of the tip sleeve 114. The proximal end 174 of the tip sleeve 114 is the proximal end of the tip 112. The lumen 172 is sized to receive the spindle 108 (visible in FIG. 2) and a second portion 223 (visible in FIG. 2) of the stent-graft prosthesis 201 (visible in FIG. 2) disposed over the spindle 108. The tip sleeve 114 further includes the plurality of tabs 152 disposed on a proximal portion 178 of the tip sleeve 114. The tip sleeve 114 is configured to retain the second portion 223 of the stent-graft prosthesis 201 in the radially compressed state for delivery to a desired treatment location. The tip sleeve 114 is further configured to release the second portion 223 of the stent-graft prosthesis 201 when the delivery catheter 102 is in the release configuration.

The plurality of tabs 152 are spaced around a circumference of the proximal portion 178 of the tip sleeve 114, as best shown in FIG. 5. In the embodiment of FIG. 5, each tab 152 is formed from the tip sleeve 114. Each tab 152 includes a first end 180 coupled to the tip sleeve 114, a second end 182 opposite the first end 180, a first side 184 and a second side 186 opposite the first side 184. The second end 182, the first side 184 and the second side 186 are each formed by detaching the second end 182, the first side 184 and the second side 186 from the tip sleeve 114. Each tab 152 includes a radially contracted state wherein the second end 182 is disposed radially inward from the first end 180. Each tab 152 is sized and spaced around the circumference of the proximal portion 178 of the tip sleeve 114 such that the deployment of the stent-graft prosthesis 201 and the locking of the spindle 108 to the tip sleeve 114 by the lock mechanism 118 is both insured and optimized. Each tab 152 is configured with a shape memory to return to the radially contracted state when not acted upon by an outside force. Mechanical shape memory may be imparted to each tab 152 by methods known in the art. For example, and not by way of limitation, each tab 152 may be formed of materials that can be made to have shape memory characteristics such as, but not limited to nickel alloys (e.g. MP35N), stainless steel, and nickel titanium alloys (e.g. NITINOL). The tabs 152 may be formed by a variety of methods, non-limiting examples of which include laser cutting, machining, or other appropriate methods. While the plurality of tabs 152 have been described an integral component of the tip sleeve 114, alternatively, each tab 152 may be formed as a separate component with the first end 180 coupled to the tip sleeve 114 by any suitable method. It will be understood that more or fewer tabs 152 may be utilized, and that the specific number of tabs 152 shown in FIG. 5. is for exemplary purposes only. Moreover, the shape of the plurality of tabs 152 as shown in FIG. 5 is not meant to be limiting, and other shapes may be utilized.

Figure 6:
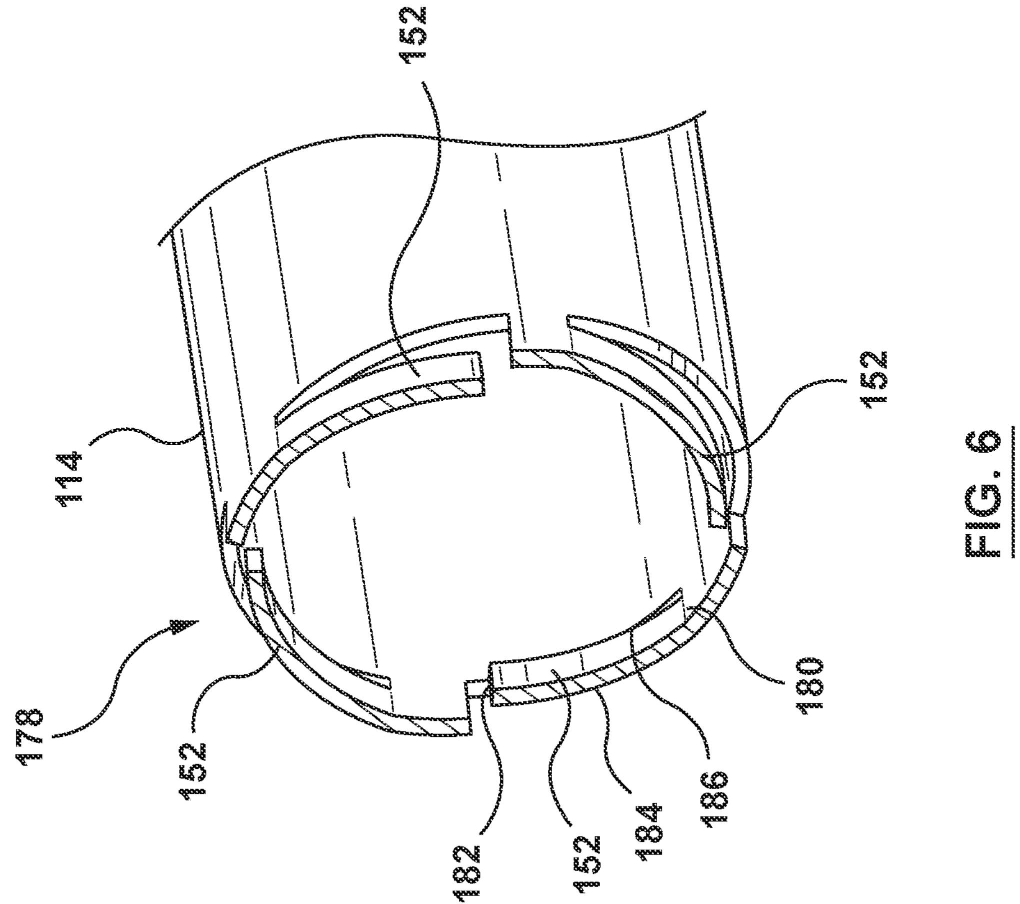
FIG. 6 depicts a perspective view of a portion of the tip sleeve of FIG. 3, wherein a distal portion of the tip sleeve has been removed for improved visibility of a plurality of tabs.
Figure 7:
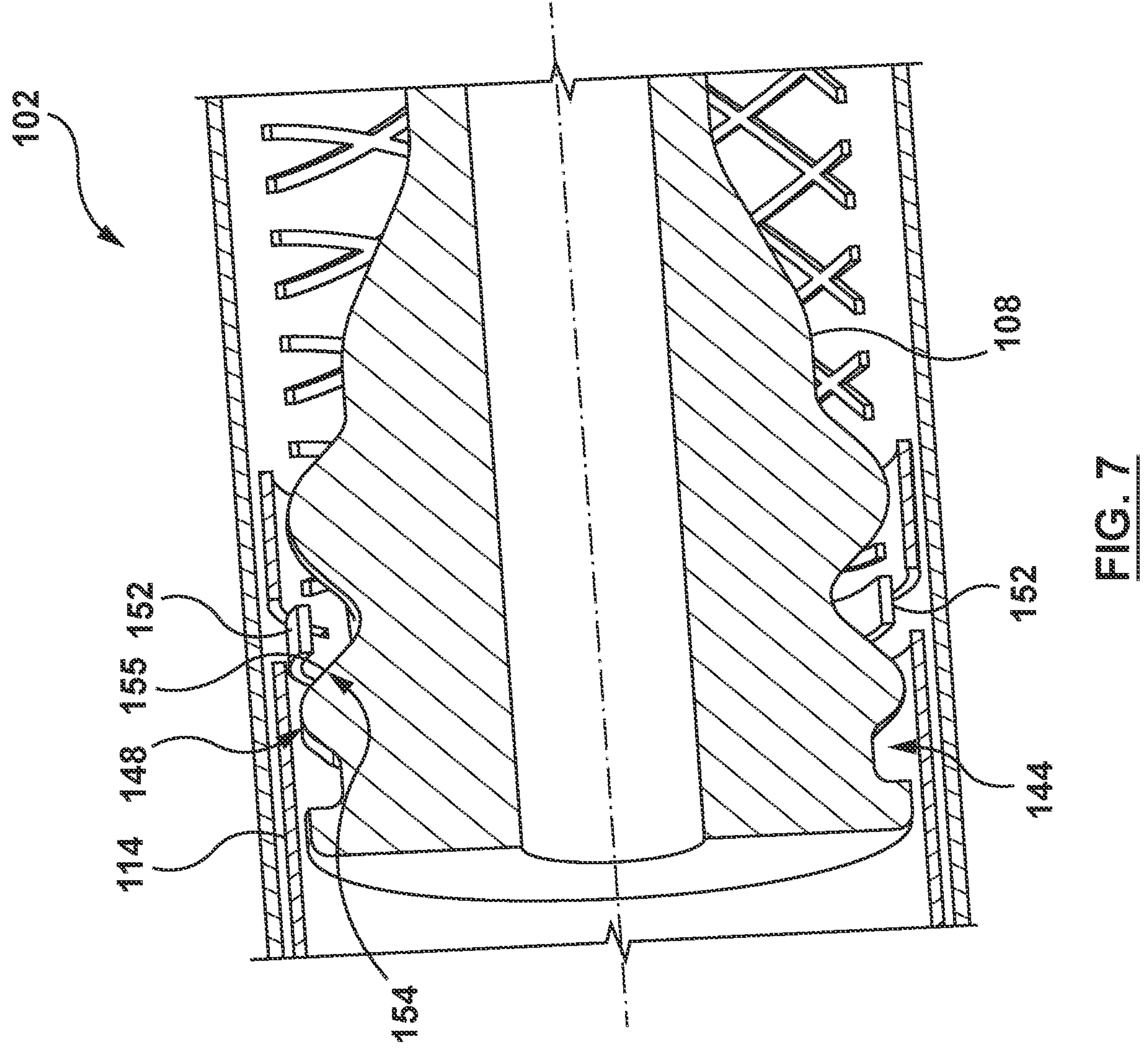
FIG. 7 depicts a longitudinal cross-sectional view of a lock mechanism of the delivery catheter of FIG. 2 taken along the longitudinal centerline of the delivery catheter, wherein the delivery catheter is in the delivery configuration.

In the embodiment of FIGS. 1-10, the lock mechanism 118, also referred to herein as a tip travel limiter, includes the plurality of tabs 152 of the proximal portion 178 of the tip sleeve 114 of FIG. 5 and the radial groove 144 of the spindle 108 of FIG. 4. The lock mechanism 118 is configured to lock the tip sleeve 114 to the spindle 108 to prevent relative longitudinal movement between the spindle 108 and the tip sleeve 114 when the delivery catheter 102 is in the release configuration. Stated another way, the lock mechanism 118 is configured to stop distal movement of the tip 112 (which includes tip sleeve 114) while actively pushing the stent graft out of the tip sleeve 114. With the delivery catheter 102 in the delivery configuration, the plurality of tabs 152 are disposed proximal of the radial groove 144 of the spindle 108, as shown in FIG. 6. As the delivery catheter 102 is transitioning from the delivery configuration to the release configuration, the tip sleeve 114 and the plurality of tabs 152 disposed thereon move or translate distally. During the distal advancement of the tip sleeve 114, each tab 152 travels over the outer surface 155 of the outer shoulder 154 of the proximal wall 148 of the spindle 108. More specifically, each tab 152 is deflected radially outward by the outer shoulder 154 as the tab 152 travels distally over the outer surface 155 of the outer shoulder 154. Once each tab 152 has traversed the proximal wall 148 and is disposed over the radial groove 144, the shape memory properties, described previously herein, of each tab 152 returns each tab 152 to the radially contracted state, with the second end 182 of each tab 152 disposed or engaged within the radial groove 144, as shown in FIG. 7. The inner shoulders 149, 153 of the proximal and distal walls 148, 180, respectively, are each of a sufficiently steep angle in relation to a central longitudinal axis $LA_s$ of the spindle 108 that each tab 152 is prevented from deflecting or moving out of the radial groove 144 once disposed therein. Thus, with each tab 152 extended into the radial groove 144, the tip sleeve 114 is locked to the spindle 108 and the lock mechanism 118 prevents relative longitudinal movement between the spindle 108 and the tip sleeve 114.

With an understanding of the components of the prosthesis delivery system 100, it is now possible to describe their interaction to deliver and release the stent-graft prosthesis 201 at a desired treatment location and to limit the longitudinal travel of the tip sleeve 114 of the tip 112 relative to the spindle 108.

Figure 9:
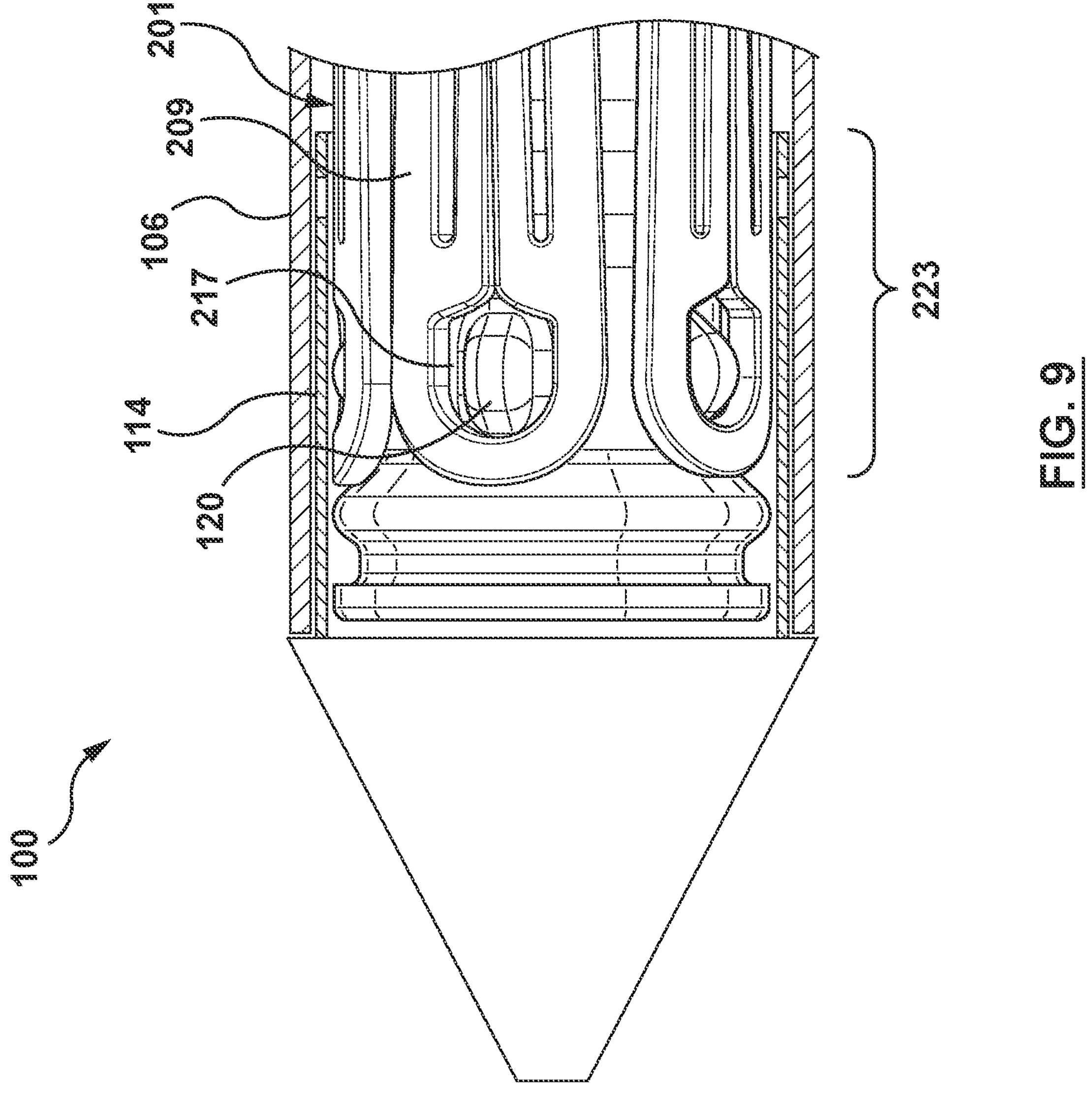
FIG. 9 depicts a side view of a distal portion of the prosthesis delivery system of FIG. 1, wherein the delivery catheter is in a delivery configuration and a portion of an outer sheath of the delivery catheter is transparent for clarity.

The stent-graft prosthesis 201 in the radially compressed configuration is loaded onto the delivery catheter 102. More precisely, the first portion 221 of the stent-graft prosthesis 201 is retained in the radially compressed state by the outer sheath 106 of the delivery catheter 102, as shown previously in FIG. 2. As best shown in FIG. 9, each opening 217 of the proximal bare stent 209 of the stent-graft prosthesis 201 is disposed over a corresponding spindle pin 120 and the second portion 223 of the stent-graft prosthesis 201 is retained in the radially compressed state by the tip sleeve 114. Thus, the stent-graft prosthesis 201 is retained in the radially compressed configuration by the delivery catheter 102 in the delivery configuration.

Once the prosthesis delivery system 100 is advanced to the desired treatment location, the outer sheath 106 is retracted proximally to release the first portion 221 of the stent-graft prosthesis 201, and the first portion 221 of the stent-graft prosthesis 201 returns to the radially expanded state. As described above, the delivery catheter is in a partial release configuration at this stage in the method of use.

Figure 10:
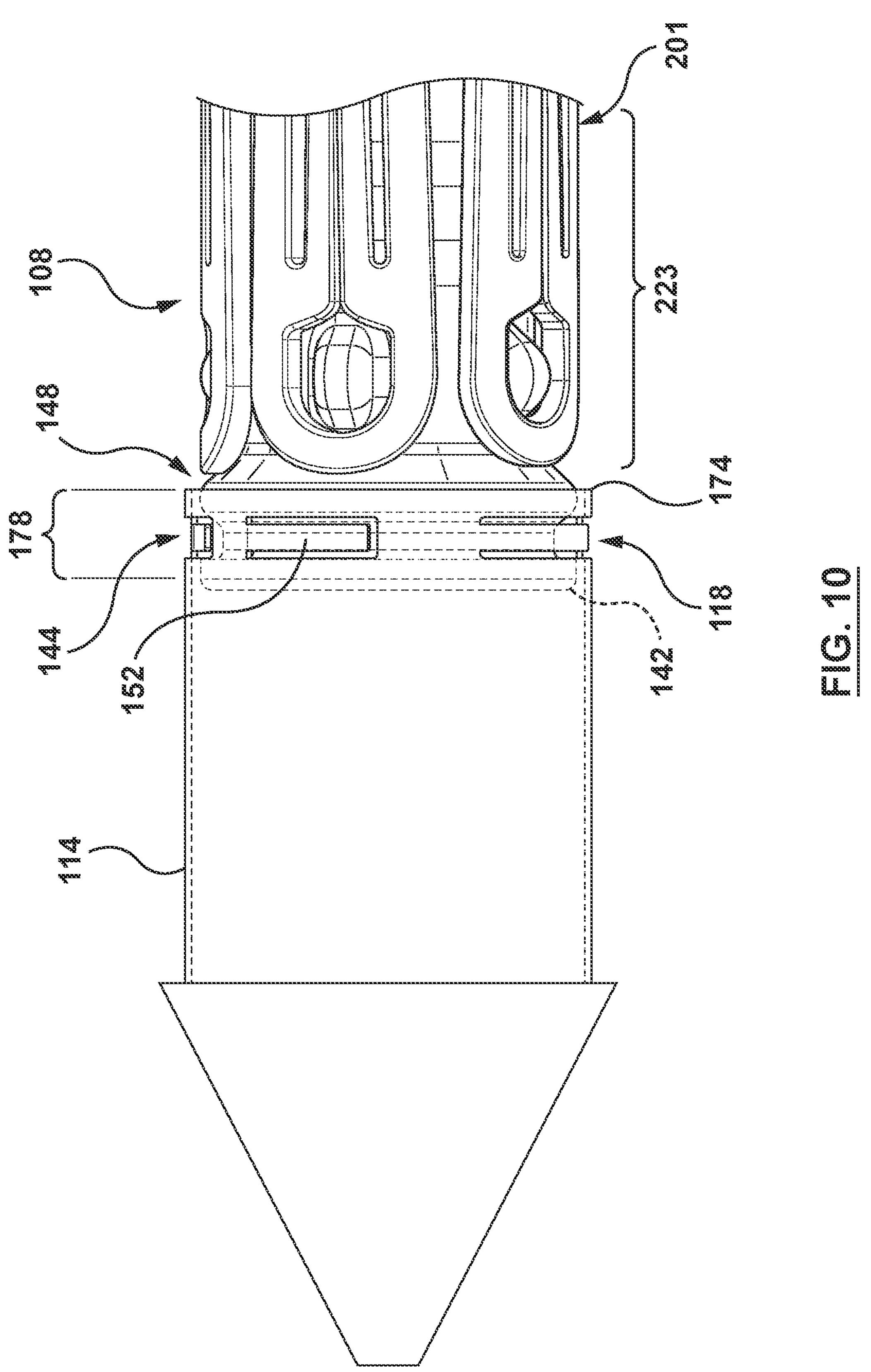
FIG. 10 depicts a side view of the distal portion of the prosthesis delivery system of FIG. 1, wherein the delivery catheter is in a release configuration and a portion of an outer sheath of the delivery catheter is transparent for clarity.

Next, the inner shaft 116 (visible in FIG. 2) is advanced distally, and the tip sleeve 114 travels distally in relation to the spindle 108 to release the second portion 223 of the stent-graft prosthesis 201, as shown in FIG. 10. The second portion 223 of the stent-graft prosthesis 201 returns to the radially expanded state. Thus, the stent-graft prosthesis 201 has fully or completely transitioned from the radially compressed configuration to the radially expanded configuration.

The inner shaft 116 is advanced distally until each tab 152 of the tip sleeve 114 travels over the proximal wall 148 of the spindle 108 and each tab 152 returns to the radially contracted state extending into the radial groove 144, as shown in FIG. 10. Once disposed within the radial groove 144, the plurality of tabs 152 prevent relative longitudinal movement between the spindle 108 and the tip sleeve 114. Thus, the lock mechanism 118 locks the spindle 108 to the tip sleeve 114 when the delivery catheter 102 is in the release configuration.

The delivery catheter 102 is configured such that when in the release configuration of FIG. 10, there is no longitudinal gap between the tip sleeve 114 and the spindle 108. More precisely, when the tip sleeve 114 is advanced distally and the delivery catheter 102 transitions from the delivery configuration to the release configuration, the proximal end 174 of the tip sleeve 114 is disposed proximal of the distal end 142 of the spindle 144 such that a proximal portion of the tip sleeve 114 overlaps a distal portion of the spindle 108. Stated another way, when the delivery catheter 102 is in the release configuration, a portion of the tip sleeve 114 is disposed over the radial groove 144 of the spindle 108. Thus, there is no longitudinal gap between the tip sleeve 114 and the spindle 108 that may snag, catch or otherwise damage the stent-graft prosthesis 201 as a distal portion of the delivery catheter 102 is proximally retracted through the deployed stent-graft prosthesis 201.

Figure 11:
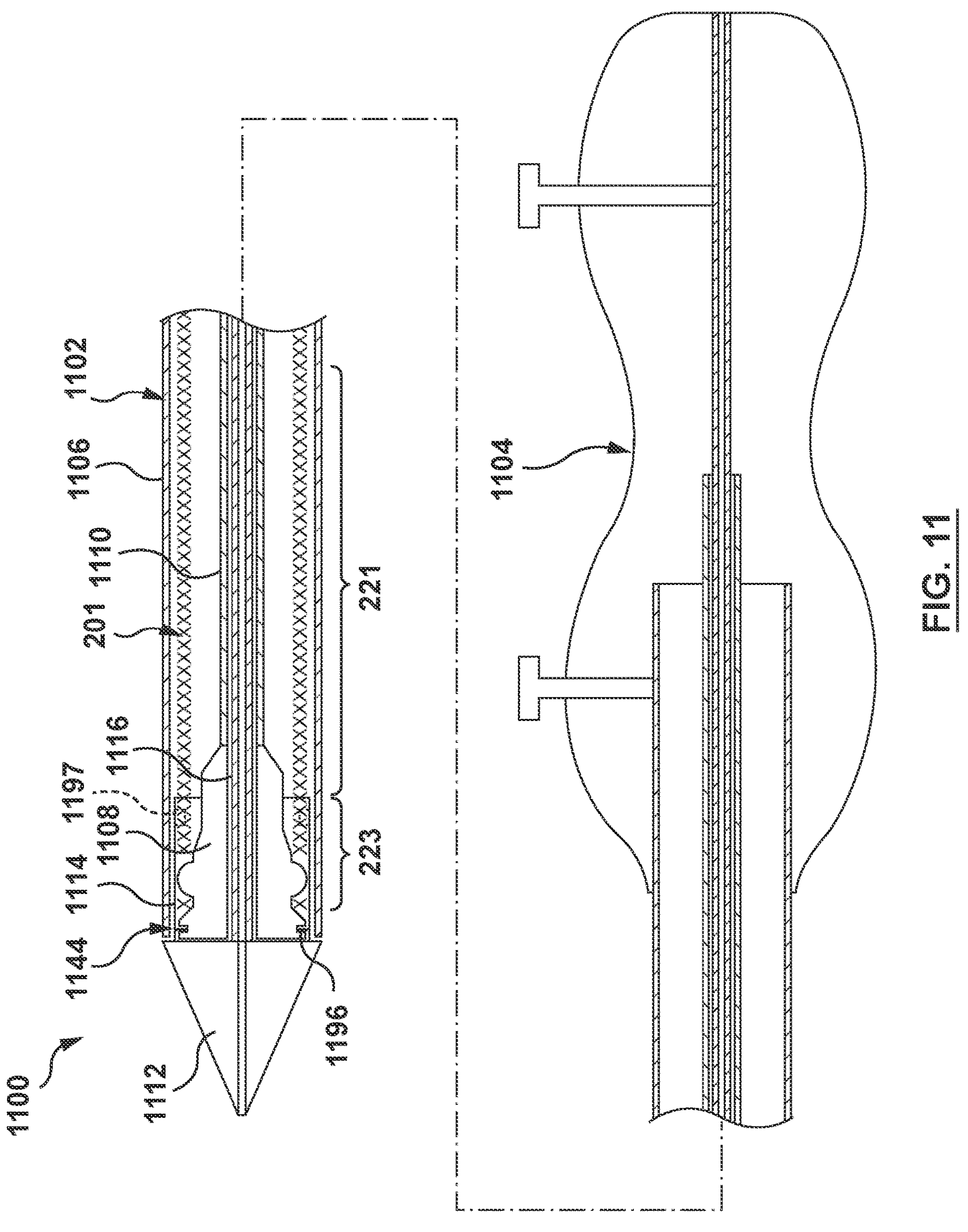
FIG. 11 depicts a longitudinal cross-sectional view of a prosthesis delivery system in accordance with another embodiment hereof, wherein a delivery catheter of the prosthesis delivery system is in a delivery configuration and a stent-graft prosthesis is in a radially compressed configuration.

FIGS. 11-17 illustrate a prosthesis delivery system 1100 having a lock mechanism with a different configuration in accordance with another embodiment hereof. As shown in FIG. 11, the prosthesis delivery system 1100, includes a delivery catheter 1102 and a stent-graft prosthesis 201 of FIG. 3. The delivery catheter 1102 includes a handle 1104, an outer sheath 1106, a spindle 1108, a spindle shaft 1110, a tip 1112 including a tapered portion 1195 and a tip sleeve 1114, an inner shaft 1116, and a lock mechanism 1118. The prosthesis delivery system 1100, the delivery catheter 1102, the handle 1104, the outer sheath 1106, the spindle 1108, the spindle shaft 1110, the tip 1112, the outer sheath 1106, and the inner shaft 1116 are similar to the prosthesis delivery system 100, the delivery catheter 102, the handle 104, the outer sheath 106, the spindle 108, the spindle shaft 110, the tapered tip 112, the tip sleeve 114, and the inner shaft 116, respectively. Therefore, similar construction details and alternatives will to be repeated. However, with the prosthesis delivery system 1100, the lock mechanism 1118 includes a radial groove 1144 in the spindle 1108, a spring mechanism 1196 disposed in the radial groove 1144, and a plurality of slots 1197 in a proximal portion 1178 of the tip sleeve 1114. The lock mechanism 1118 is configured to lock the tip sleeve 1114 to the spindle 1108 to prevent relative longitudinal movement between the spindle and the tip sleeve when the delivery catheter 1102 is in the release configuration.

Figure 12:
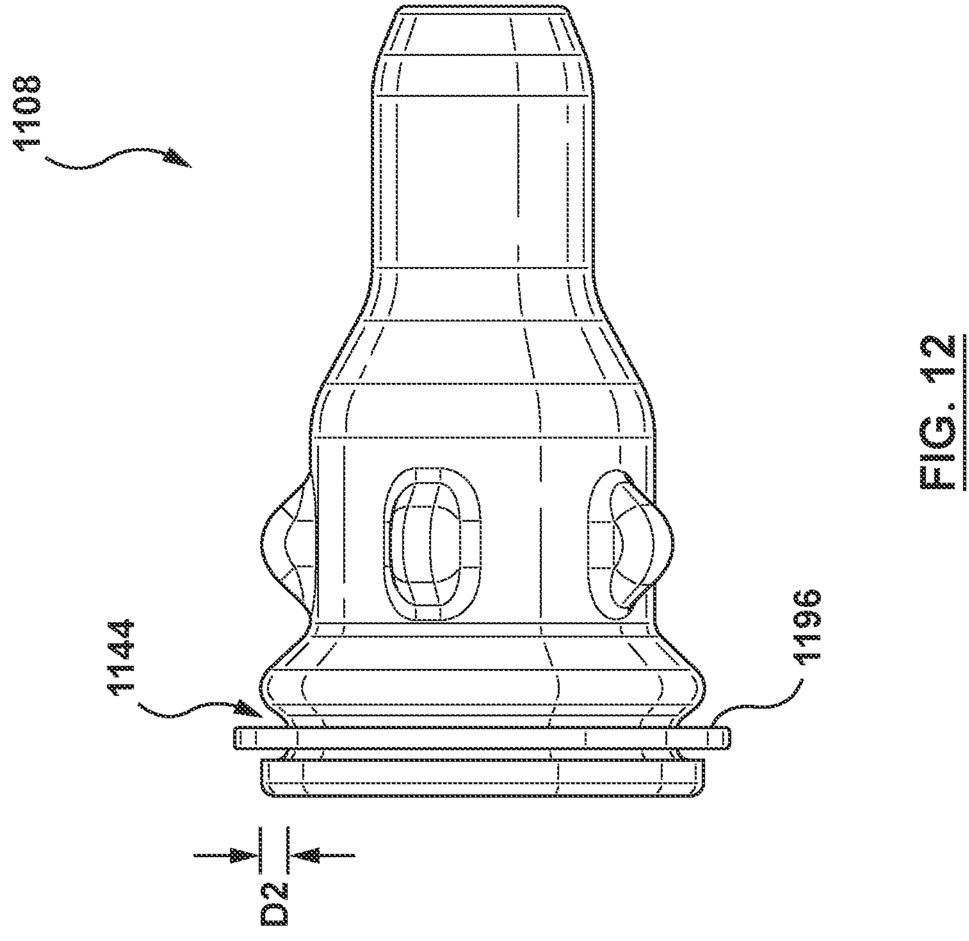
FIG. 12 depicts a side view of a spindle of the delivery catheter of FIG. 11.
Figure 13:
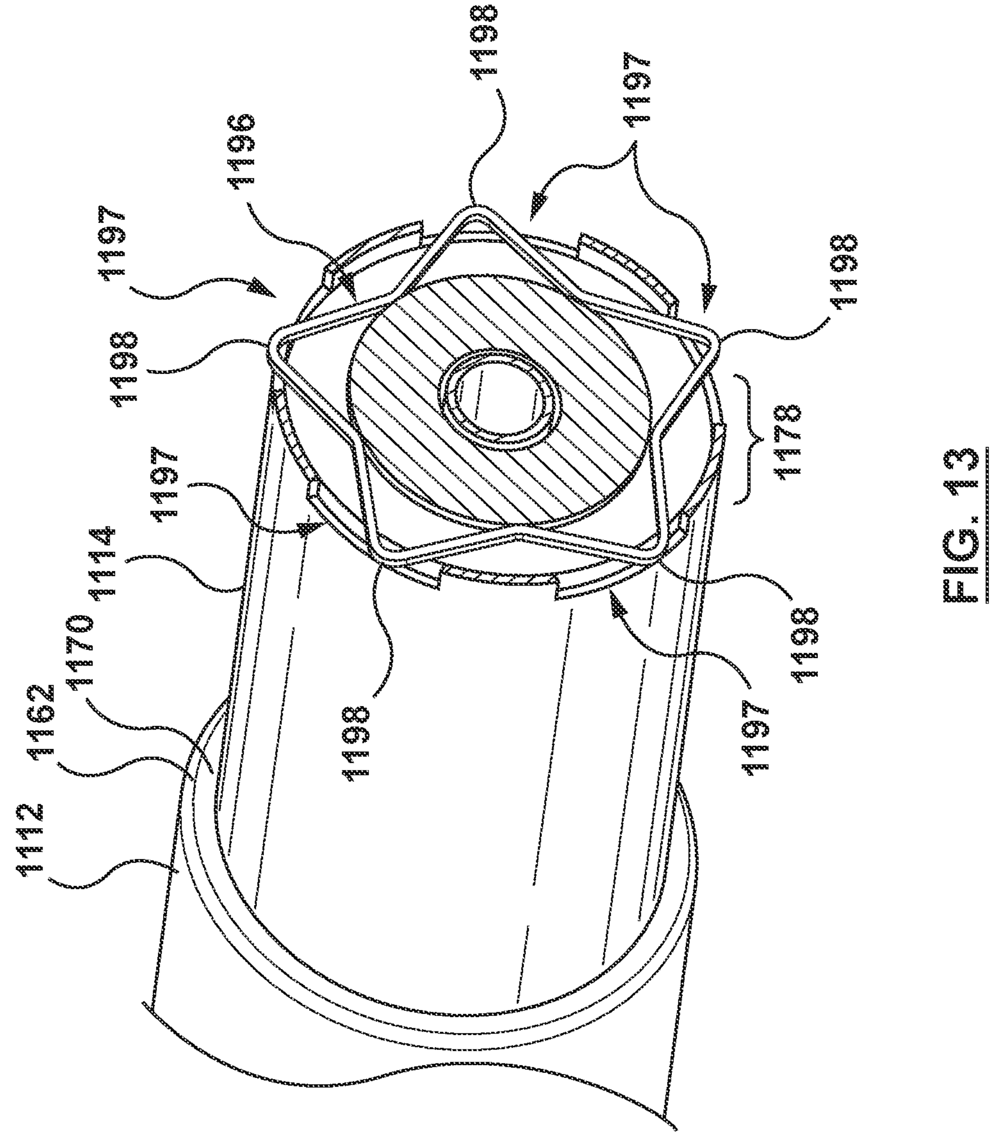
FIG. 13 depicts a partial perspective view of a lock mechanism of the delivery catheter of FIG. 11, wherein a proximal portion of a spindle and a proximal portion of a tip sleeve have been removed for clarity.
Figure 14:
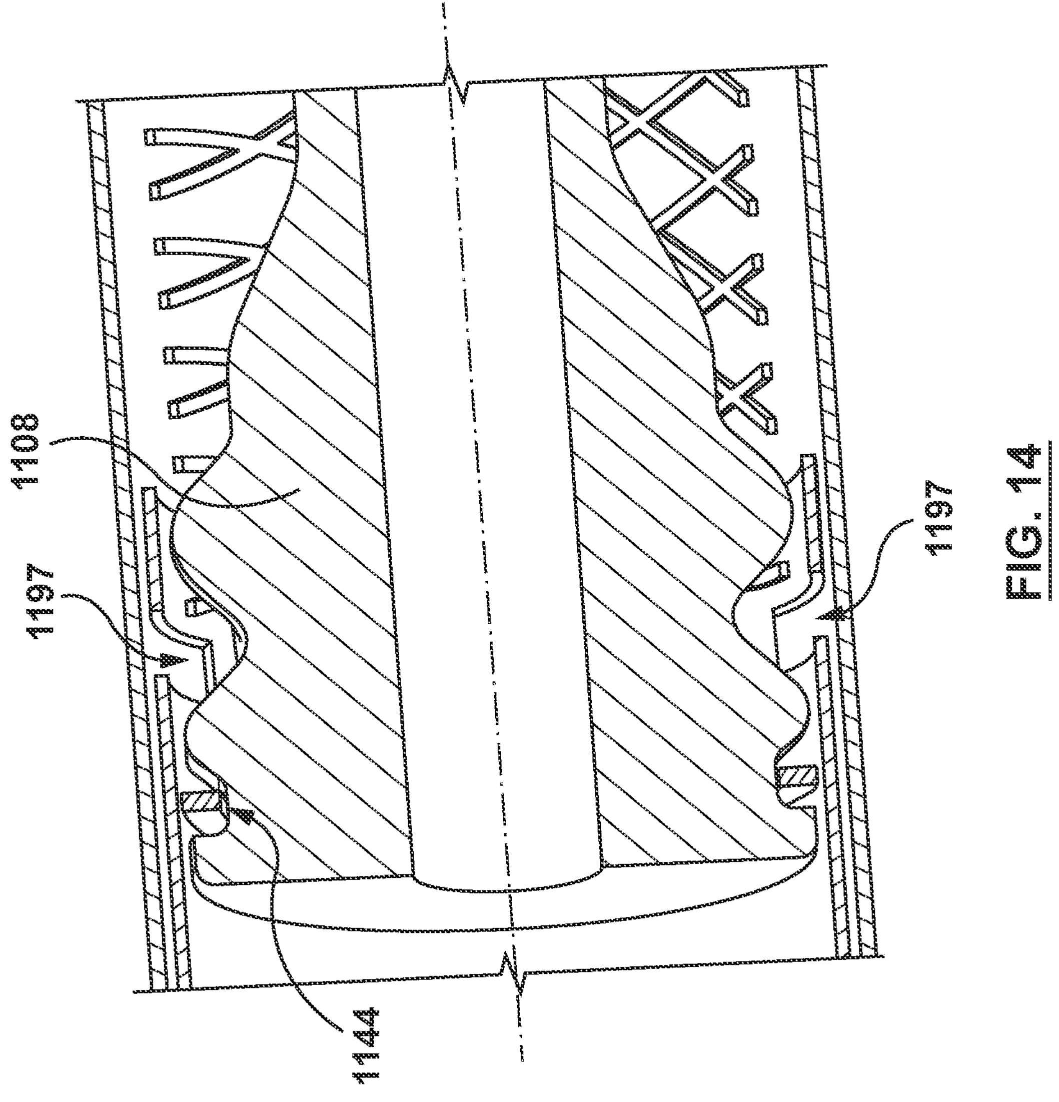
FIG. 14 depicts a longitudinal cross-sectional view of a lock mechanism of the delivery catheter of FIG. 11 taken along the longitudinal centerline of the delivery catheter, wherein the delivery catheter is in the delivery configuration.

As shown in FIG. 12, the spindle 1108 includes the radial groove 1144 and the spring mechanism 1196 disposed in the radial groove 1144. The radial groove 1144 includes a depth D2 optimized to fit/retain the spring mechanism 1196 in either a radially compressed state or a radially expanded state. The spring mechanism 1196 has the radially compressed state when the delivery catheter 1102 is in a delivery configuration, and the radially expanded state when the delivery catheter 1102 is in a release configuration. The spring mechanism 1196 is self-expanding to return to the radially expanded state from the radially compressed state. In the embodiment of FIGS. 11-17, the spring mechanism 1196 is star-shaped with five (5) points 1198 extending radially outward, as best shown in FIG. 13. However, in other embodiments, the spring mechanism 1196 may have alternate polygonal shapes with greater or fewer points 1198 such as, but not limited to a triangular shape with three (3) points, a hexagonal shape with six (6) points, or other shapes suitable for the purposes described herein. The spring mechanism 1196 may be formed of various materials including, but not limited to stainless steel, nickel-titanium alloys (e.g. NITINOL), or other suitable materials.

The tip sleeve 1114 of the tip 1112 is a generally cylindrical tube extending proximally from a proximal end 1162 and adjacent a shoulder 1170 of the tapered tip 1112, as shown in FIG. 13. The tip sleeve 1114 includes a plurality of slots 1197 spaced around a circumference of the proximal portion 1178 of the tip sleeve 1114. Each slot 1197 is configured to receive a corresponding point 1198 of the spring mechanism 1196 when the delivery catheter 1102 is in the release configuration, as shown in FIG. 13. Each slot 1197 is a radial opening in the tip sleeve 1114 of optimized size and location to enable the corresponding point 1198 of the spring mechanism 1196 to be received/engage without radial alignment of the spring mechanism 1196. Stated another way, each slot 1197 is sized such that as the tip sleeve 1114 advances distally relative to the spindle 1108, the corresponding point 1198 of the spring mechanism 1196 will pass through the corresponding slot 1197 without the clinician having to manually align the point 1198 of the spring mechanism 1196 with the corresponding slot 1197. The plurality of slots 1197 is disposed proximal of the radial groove 1144 of the spindle 1108 when the delivery catheter 1102 is in the delivery configuration of FIG. 14. The plurality of slots 1197 are disposed over the radial groove 1144 when the delivery catheter 1102 is in the release configuration of FIG. 15. The plurality of slots 1197 may be formed in the tip sleeve 1114 by methods such as, but not limited to laser cutting, machining, or other suitable methods. While shown with five (5) slots 1197, it will be understood that more or fewer slots 1197 may be utilized corresponding to the number of points 1198 of the spring mechanism 1196.

Figure 15:
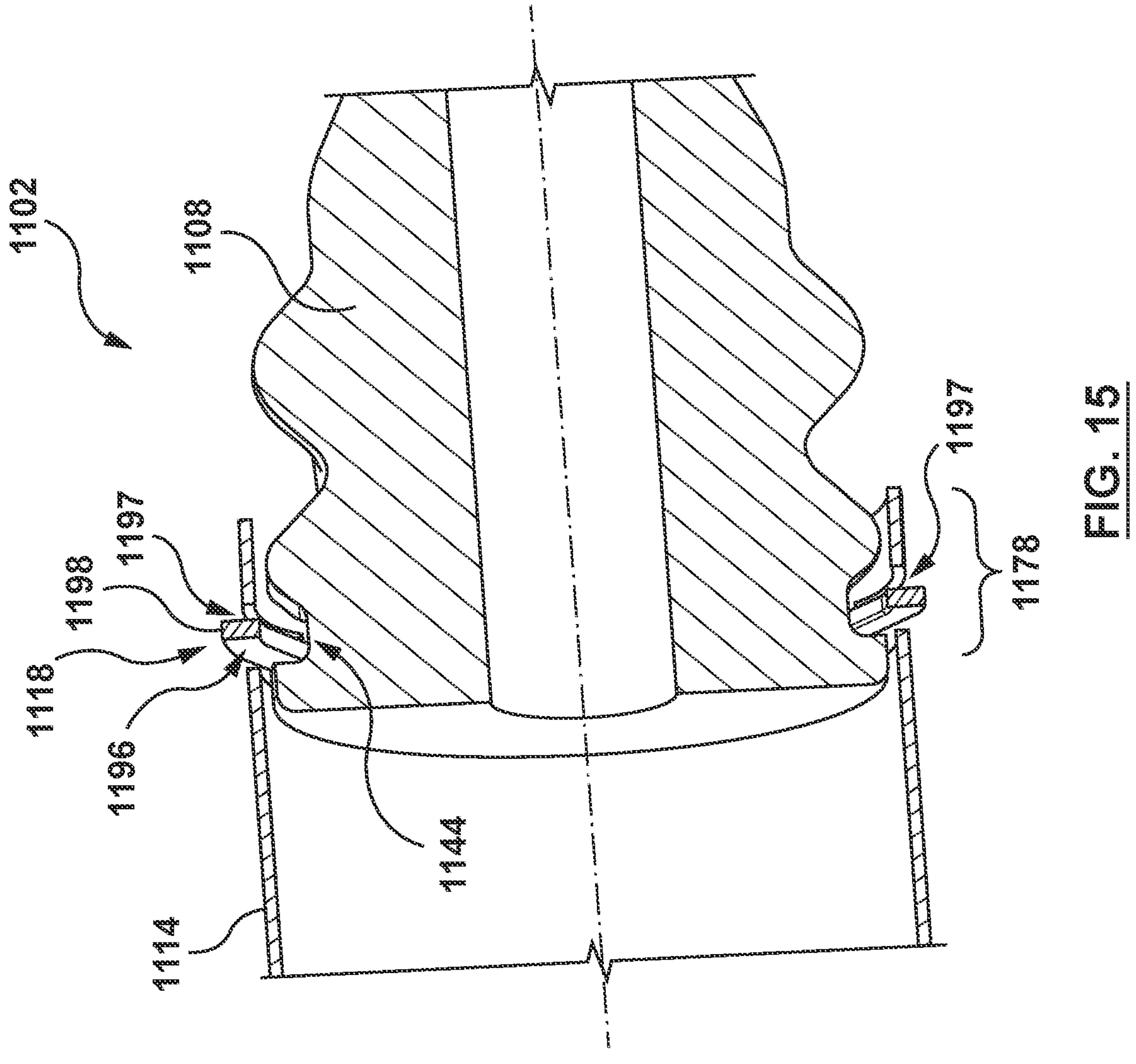
FIG. 15 depicts a longitudinal cross-sectional view of the lock mechanism of the delivery catheter of FIG. 11 taken along the longitudinal centerline of the delivery catheter, wherein the delivery catheter is in the release configuration.

In the embodiment of FIGS. 11-15, the lock mechanism 1118 includes the radial groove 1144 of the spindle 1108, the spring mechanism 1196 disposed in the radial groove 1144, and the plurality of slots 1197 of the proximal portion 1178 of the tip sleeve 1114, as best shown in FIG. 15. The lock mechanism 1118 is configured to lock the tip sleeve 1114 to the spindle 1108 to prevent relative longitudinal movement between the spindle 1108 and the tip sleeve 1114 when the delivery catheter 1102 is in the release configuration.

Figure 16:
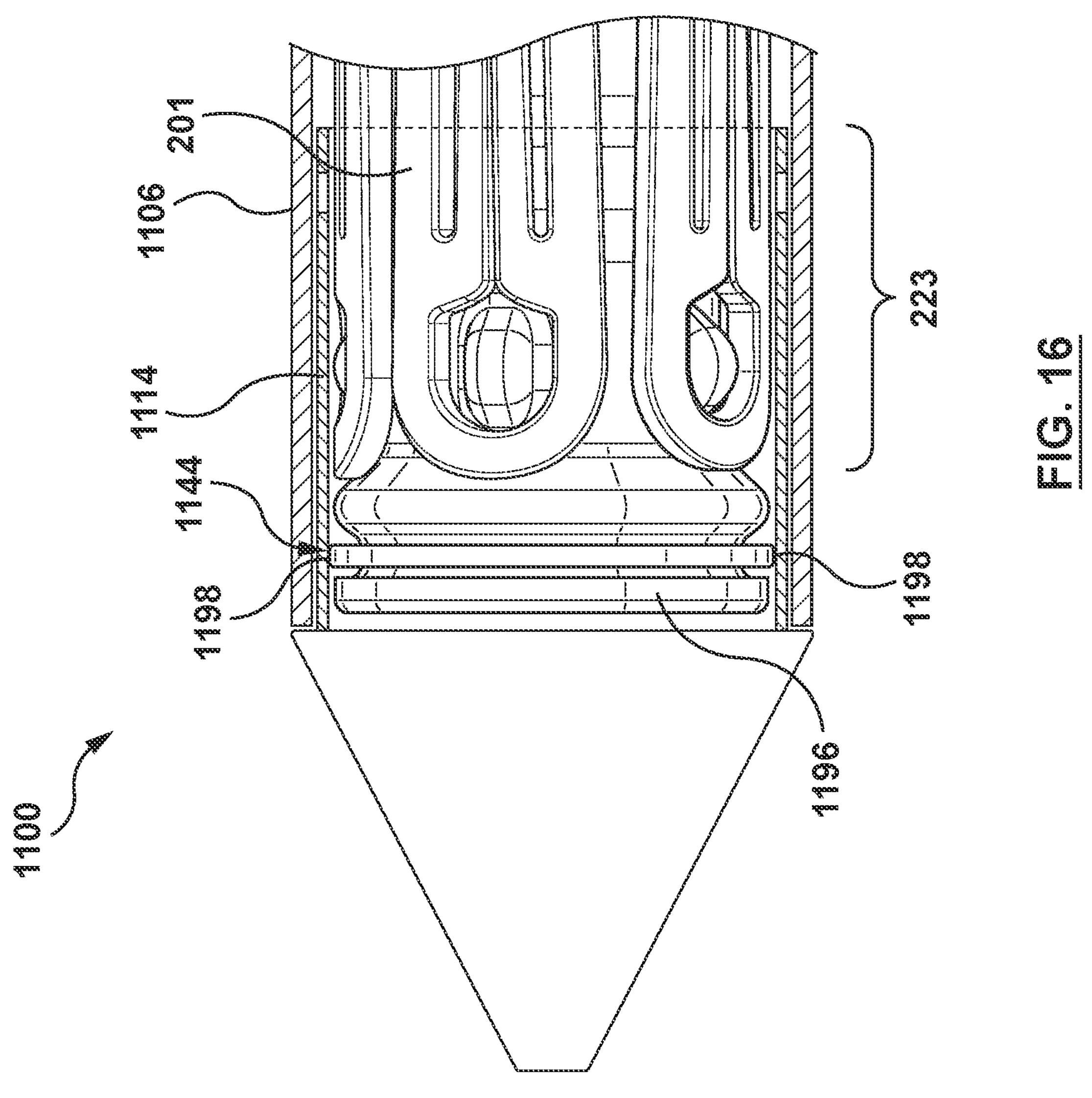
FIG. 16 depicts a side view of a distal portion of the prosthesis delivery system of FIG. 11, wherein the delivery catheter is in a delivery configuration and a portion of an outer sheath of the delivery catheter is transparent for clarity.
Figure 17:
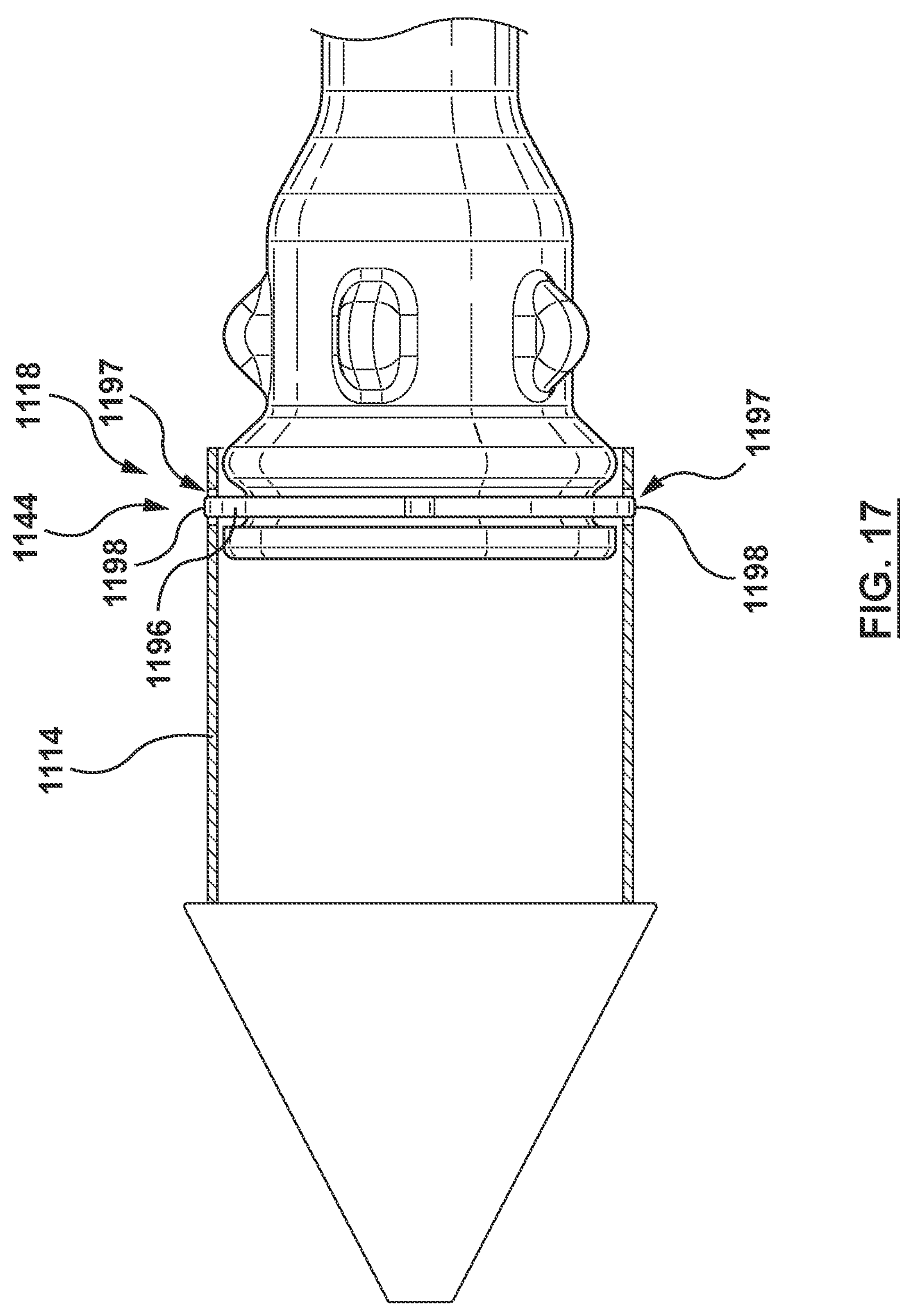
FIG. 17 depicts a side view of the distal portion of the prosthesis delivery system of FIG. 11, wherein the delivery catheter is in a release configuration and a portion of an outer sheath of the delivery catheter is transparent for clarity.

The interaction of the components of the prosthesis delivery system 1100 may now be described with reference to FIGS. 16-17. FIG. 16 shows a distal portion of the delivery catheter 1102 in the delivery configuration, with the stent-graft prosthesis 201 in the radially compressed configuration loaded onto the delivery catheter 1102. In the delivery configuration, an inner surface of the tip sleeve 1114 of the delivery catheter 1102 pushes radially inward on the plurality of points 1198 to radially compress the spring mechanism 1196 to the radially compressed state within the radial groove 1144.

Once the prosthesis delivery system 1100 is positioned at the desired treatment location, the outer sheath 1106 is retracted proximally to release a first portion 221 (visible in FIG. 11) of the stent-graft prosthesis 201. The first portion 221 (visible in FIG. 11) of the stent-graft prosthesis 201 returns to the radially expanded state. Next, with a second portion 223 of the stent-graft prosthesis 201 retained in a radially compressed state by the tip sleeve 1114, as shown in FIG. 16, the inner shaft 1116 (visible in FIG. 11) is advanced distally. Advancement of the inner shaft 1116 (visible in FIG. 11) advances the tip sleeve 1114 distally in relation to the spindle 1108. The inner shaft 1116 is advanced distally to release the second portion 223 of the stent-graft prosthesis 201, and when released, the second portion 223 of the stent-graft prosthesis 201 returns to the radially expanded state.

The tip sleeve 1114 is advanced distally until the plurality of slots 1197 is disposed over the radial groove 1144 and the spring mechanism 1196 disposed therein is released. When released, the spring mechanism 1196 returns to the radially expanded state and each point 1198 of the spring mechanism 1196 extends radially outward and engages or extends through the corresponding slot 1197 of the tip sleeve 1114, as shown in FIG. 17. With each point 1198 engaged or disposed through the corresponding slot 1197, the spindle 1108 is locked to the tip sleeve 1114 by the lock mechanism 1118 and relative movement between the spindle 1108 and the tip sleeve 1114 is prevented.

Thus, when the delivery catheter 1102 is in the release configuration, the proximal portion 1178 of the tip sleeve 1114 is disposed over the radial groove 1144 of the spindle 1108 and there is no longitudinal gap between the tip sleeve 1114 and the spindle 1108 that may snag, catch or otherwise damage the stent-graft prosthesis 201 as a distal portion of the delivery catheter 1102 is proximally retracted through the deployed stent-graft prosthesis 201.

Although the embodiments of FIGS. 1-10 and FIGS. 11-17 have been described with specific lock mechanisms to limit tip travel and lock a delivery catheter in a release configuration, this is not meant to be limiting, and other lock mechanisms may be utilized. For example, a lock mechanism may include a spring ring disposed within a radial groove in a spindle, and a circumferential groove in an inner surface of a tip sleeve. When the circumferential groove is disposed over the spring ring, the spring ring may radially expand within the circumferential groove to limit tip travel and lock the delivery catheter in the release configuration.

Figure 8:
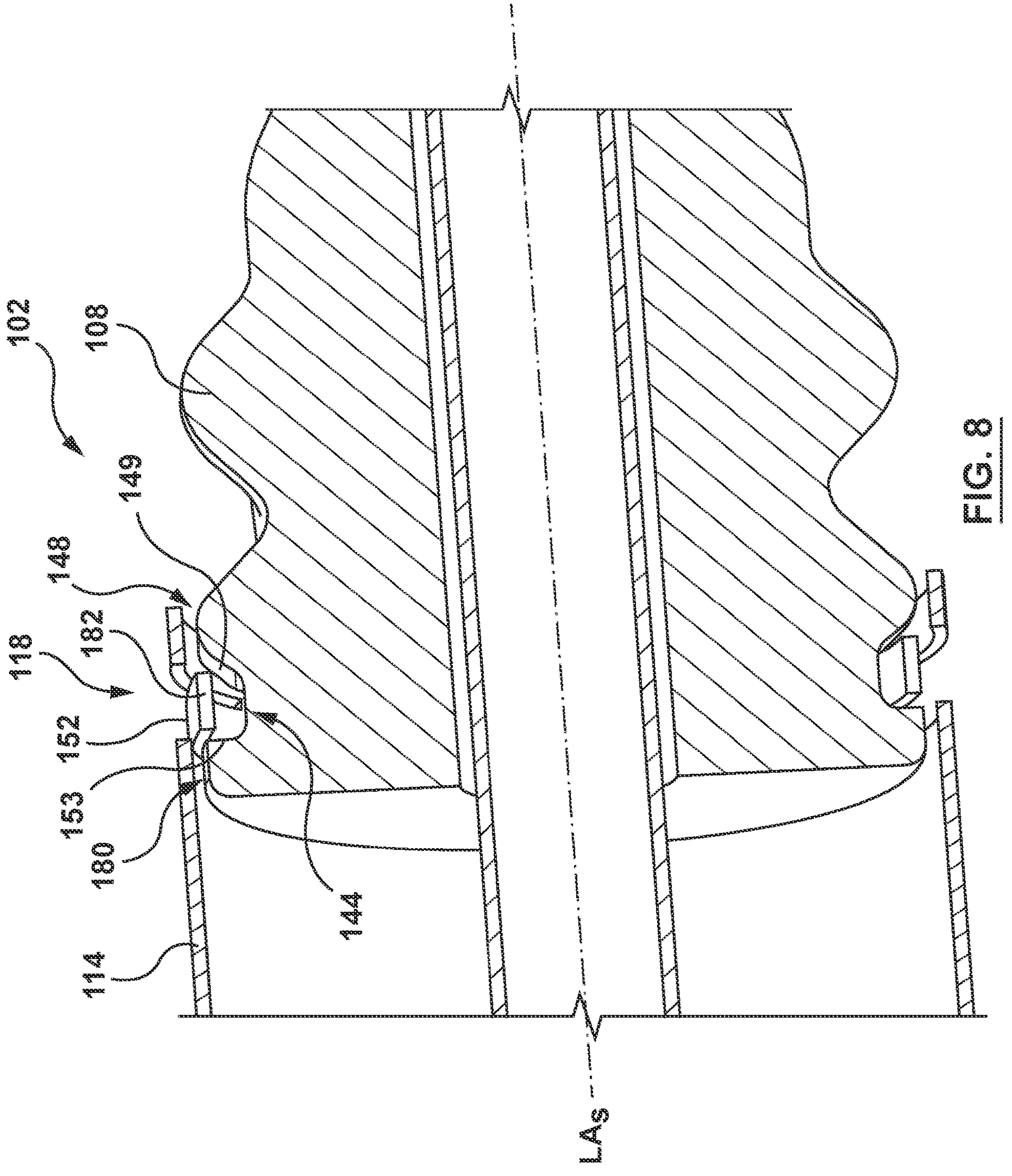
FIG. 8 depicts a longitudinal cross-sectional view of the lock mechanism of the delivery catheter of FIG. 2 taken along the longitudinal centerline of the delivery catheter, wherein the delivery catheter is in the release configuration.
Figure 18:
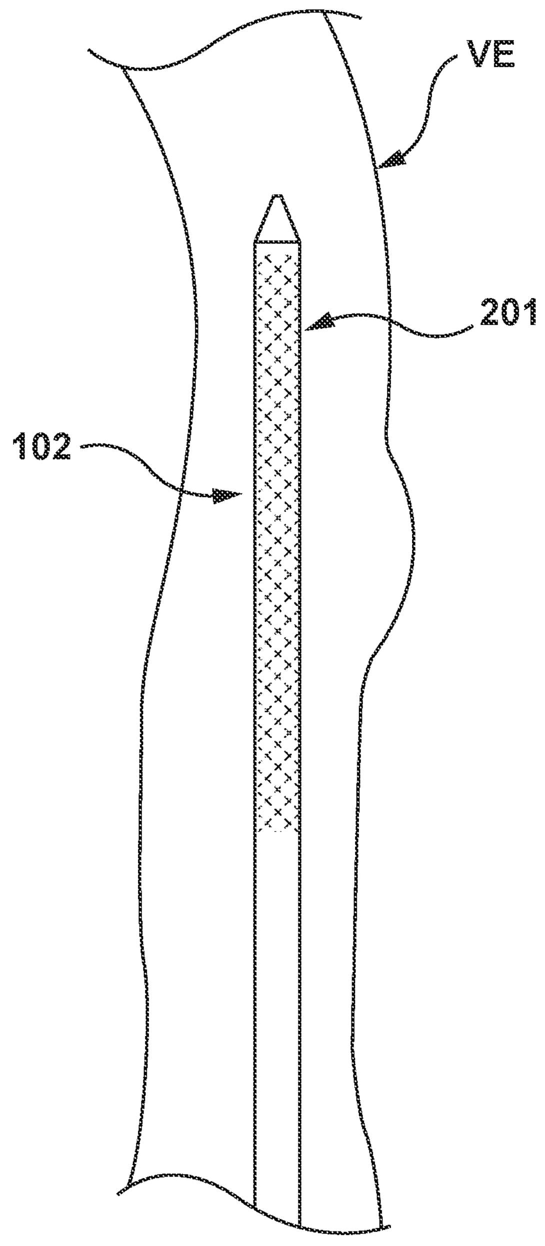
FIG. 18 depicts a sectional cut-away view of a vessel illustrating a method step of using the prosthesis delivery system of FIG. 1 to deliver and position a stent-graft prosthesis within the vessel in accordance with an embodiment hereof, wherein the prosthesis delivery system is shown having been advanced to a desired treatment site adjacent an aneurysm.

FIGS. 18-21 are sectional cut-away views of a vessel VE illustrating a method of delivering and releasing a stent-graft prosthesis 201 of FIG. 8 in accordance with an embodiment hereof. With reference to FIG. 18, the stent-graft prosthesis 201 has been loaded onto the delivery catheter 102 and is shown positioned at a desired treatment location of an aneurysm AN within the vessel VE. The stent-graft prosthesis 201 is held in the radially compressed configuration by the delivery catheter 102. Intravascular access to the vessel VE may be achieved via a percutaneous entry point for example, in a femoral artery, using for example, the Seldinger technique, extending through the vasculature to the desired treatment location. As will be understood, a handle (not shown in FIGS. 18-21), as well as a length of the delivery catheter 102 are exposed external of the patient for access and manipulation by a clinician, even as the stent-graft prosthesis 201 is positioned at the desired treatment location. Although not shown in FIG. 18, optionally, a guidewire and/or a guide catheter may be utilized with the delivery catheter 102, with the delivery catheter 102 slidably advanced over the guidewire and/or within the guide catheter.

Figure 19:
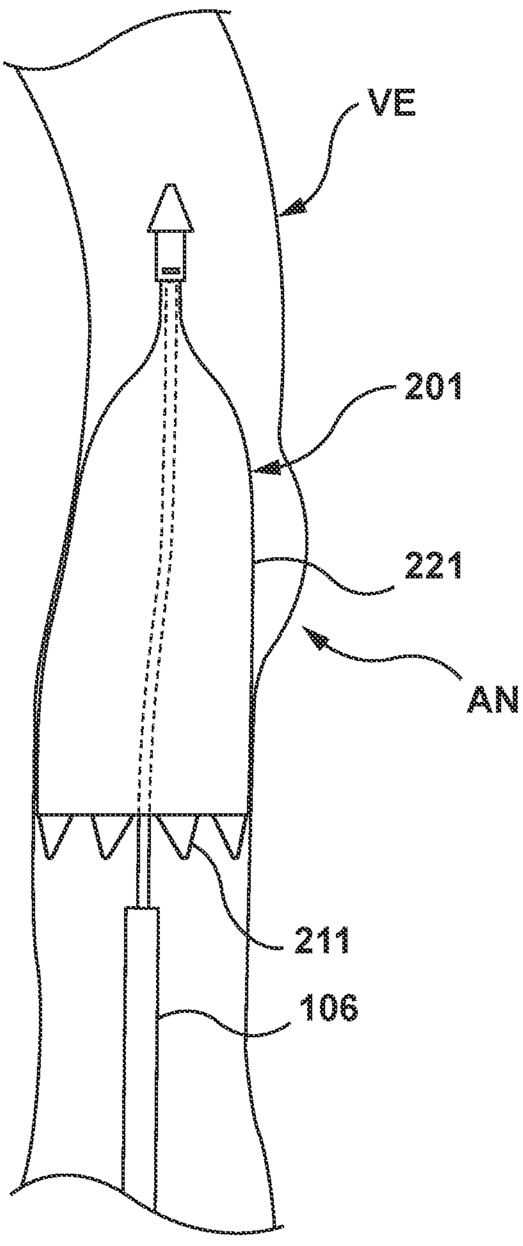
FIG. 19 is a sectional cut-away view of the vessel illustrating a method step of using the prosthesis delivery system of FIG. 1 to deliver and position a stent-graft prosthesis within the vessel in accordance with an embodiment hereof, wherein an outer sheath of a delivery catheter has been retracted proximally and a first portion of the stent-graft prosthesis has been released to an expanded state.

Once the stent-graft prosthesis 201 in the radially compressed configuration is positioned at the desired treatment location, the outer sheath 106 is manipulated or retracted proximally to release a first portion 221 of the stent-graft prosthesis 201. When released, the first portion 221 of the stent-graft prosthesis 201 expands from the radially compressed state to the radially expanded state. As the first portion 221 of the stent-graft prosthesis 201 expands, the distal bare stent 211 of the stent-graft prosthesis 201 engages a wall of the vessel VE distal of the aneurysm AN, as shown in FIG. 19.

Figure 20:
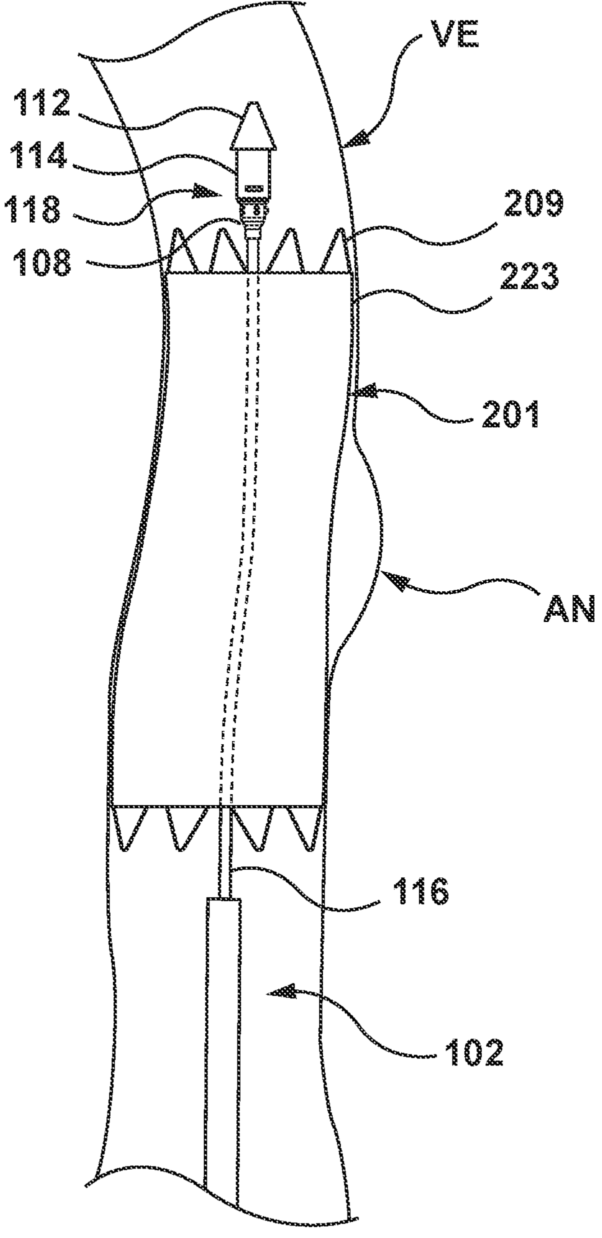
FIG. 20 is a sectional cut-away view of the vessel illustrating a method step of using the prosthesis delivery system of FIG. 1 to deliver and position a stent-graft prosthesis within the vessel in accordance with an embodiment hereof, wherein an inner shaft of the delivery catheter has been advanced distally, a tip sleeve and a spindle of the delivery catheter are locked together, and a second portion of the stent-graft prosthesis has been released to an expanded state.

In a next method step, the inner shaft 116 of the delivery catheter 102 is manipulated or advanced distally to release a second portion 223 of the stent-graft prosthesis 201. When released, the second portion 223 of the stent-graft prosthesis 201 expands from a radially compressed state to a radially expanded state and the proximal bare stent 209 of the stent-graft prosthesis 201 engages the wall of the vessel VE proximal of the aneurysm AN, as shown in FIG. 20. The inner shaft 116 is advanced distally until the lock mechanism 118 engages such that the tip sleeve 114 of the tip 112 is coupled or locked to the spindle 108 and the delivery catheter 102 has transitioned to the release configuration.

Figure 21:
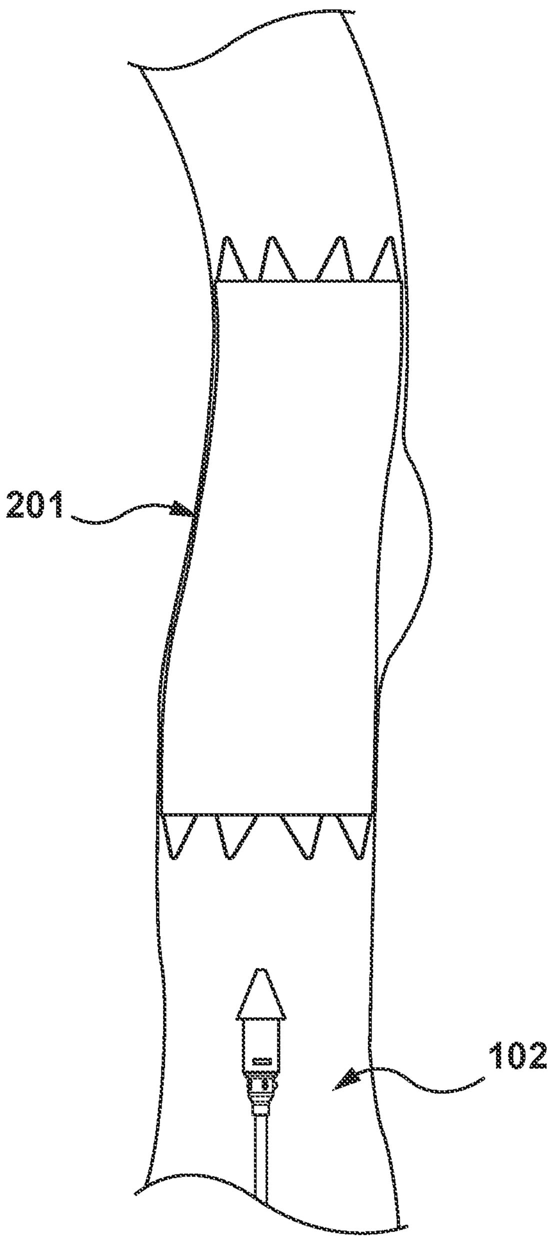
FIG. 21 is a sectional cut-away view of the vessel illustrating a method step of using the prosthesis delivery system of FIG. 1 to deliver and position a stent-graft prosthesis within the vessel in accordance with an embodiment hereof, wherein delivery catheter has been retracted proximally through the stent-graft prosthesis.

Following the deployment of the stent-graft prosthesis 201, the delivery catheter 102 is retracted proximally through the stent-graft prosthesis 201 in the radially expanded configuration, as shown in FIG. 21.

While the method of FIGS. 18-21 is described utilizing the prosthesis delivery system 100, it will be understood that the method may be utilized for other embodiments of the invention including, but not limited to the prosthesis delivery system 1100.

While various embodiments have been described above, it should be understood that they have been presented only as illustrations and examples of the present invention, and not by way of limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein can be used in combination with the features of any other embodiment.

What is claimed is:

1. A prosthesis delivery system comprising:

a prosthesis comprising at least one stent and a graft material, wherein the prosthesis has a radially compressed configuration for delivery through a vasculature and a radially expanded configuration for deployment; and a delivery catheter having a delivery configuration and a release configuration, the delivery catheter including:

a tip including a tapered portion and a tip sleeve extending proximally, wherein the tip sleeve is configured to retain a proximal portion of the prosthesis in a radially compressed state in the delivery configuration for delivery to a treatment location;

a spindle including a plurality of spindle pins;

a lock, wherein the lock locks the tip sleeve to the spindle to prevent relative longitudinal movement between the spindle and the tip sleeve when the delivery catheter is in the release configuration;

an outer sheath configured to retain a distal portion of the prosthesis in a radially compressed state in the delivery configuration for delivery to a treatment location;

an inner shaft coupled to the tip and extending proximally through the spindle to an actuator at a proximal portion of the prosthesis delivery system; and a spindle shaft coupled to the spindle and disposed around the inner shaft, wherein the inner shaft is longitudinally slidable relative to the spindle shaft with the prosthesis delivery system in the delivery configuration.

2. The prosthesis delivery system of claim 1, wherein in the delivery configuration the tip sleeve covers the spindle pins of the spindles, and in the release configuration a proximal end of the tip sleeve is distal of the spindle pins, wherein the lock locks the prosthesis delivery system in the release configuration.

3. The prosthesis delivery system of claim 2, wherein each spindle pin of the plurality of spindle pins includes a smooth, radiused and/or curved profile.

4. The prosthesis delivery system of claim 1, wherein the lock comprises a radial groove in the spindle distal of the spindle pins and at least one tab on a proximal portion of the tip sleeve, wherein in the delivery configuration the at least one tab is proximal of the radial groove of the spindle, and wherein in the release configuration the at least one tab extends radially into the radial groove of the spindle.

5. The prosthesis delivery system of claim 4, wherein the at least one tab comprises a plurality of tabs spaced around a circumference of the tip sleeve, and wherein in the release configuration, each of the plurality of tabs extend into the radial groove.

6. The prosthesis delivery system of claim 1, wherein the lock includes a radial groove in the spindle, a spring disposed in the radial groove, and at least one slot in a proximal portion of the tip sleeve, wherein in the delivery configuration, a distal portion of the tip sleeve is disposed over the radial groove in the spindle and compresses the spring into the radial groove, and wherein in the release configuration, the at least one slot of the proximal portion of the tip sleeve is disposed over the radial groove in the spindle such that a portion of the spring extends through the slot to lock the spindle and the tip sleeve together.

7. The prosthesis delivery system of claim 6, wherein in the spring is a star shaped spring with a plurality of points extending radially outwardly, wherein in the delivery configuration, the distal portion of the tip sleeve pushes the plurality of points radially inwardly to radially compress the spring into the radial groove, and wherein in the release configuration, the plurality of points extends radially outwardly through the slot in the proximal portion of the tip sleeve.

8. The prosthesis delivery system of claim 7, wherein the tip sleeve includes a plurality of slots spaced around a circumference of the proximal portion of the tip sleeve, and wherein in the release configuration each of the plurality of points of the star shaped spring extends through a corresponding one of the plurality of slots.

9. The prosthesis delivery system of claim 1, wherein with the prosthesis delivery system in the delivery configuration, the actuator is configured to push the inner shaft distally with respect to the spindle shaft such that the tip and the tip sleeve move distally relative to the spindle until the proximal portion of the tip sleeve is distal of the spindle pins and the lock locks the prosthesis delivery system in the release configuration.

10. The prosthesis delivery system of claim 1, wherein the lock is a mechanical lock that locks the tip sleeve to the spindle to prevent relative longitudinal movement between the spindle and the tip sleeve when the delivery catheter is in the release configuration.

11. The prosthesis delivery system of claim 1, wherein in the delivery configuration the tip sleeve covers the spindle pins of the spindle, and in the release configuration a proximal end of the tip sleeve is distal of the spindle pins and covers a distal portion of the spindle.

* * * * *